(12) United States Patent
Finkel

(10) Patent No.: US 10,555,687 B2
(45) Date of Patent: Feb. 11, 2020

(54) APPARATUS AND METHOD FOR PHYSIOLOGIC AND PHARMACODYNAMIC ASSESSMENT AND MONITORING

(71) Applicant: CHILDREN'S NATIONAL MEDICAL CENTER, Washington, DC (US)

(72) Inventor: Julia C Finkel, Washington, DC (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 563 days.

(21) Appl. No.: 15/290,817

(22) Filed: Oct. 11, 2016

(65) Prior Publication Data

US 2017/0100061 A1 Apr. 13, 2017

Related U.S. Application Data

(60) Provisional application No. 62/284,787, filed on Oct. 9, 2015.

(51) Int. Cl.
*A61B 5/103* (2006.01)
*A61B 5/00* (2006.01)
(Continued)

(52) U.S. Cl.
CPC .......... *A61B 5/103* (2013.01); *A61B 3/0025* (2013.01); *A61B 3/112* (2013.01); *A61B 5/0059* (2013.01);
(Continued)

(58) Field of Classification Search
CPC ..... A61B 5/103; A61B 5/0059; A61B 5/1104; A61B 5/1107; A61B 5/4824; A61B 3/0025; A61B 3/112; A61B 3/113; A61B 3/145

See application file for complete search history.

(56) References Cited

U.S. PATENT DOCUMENTS

2009/0174865 A1* 7/2009 Privitera ............... A61B 3/112
351/246
2011/0245708 A1* 10/2011 Finkel .................. A61B 5/0484
600/544

(Continued)

FOREIGN PATENT DOCUMENTS

EP 2 417 901 A1 2/2012

OTHER PUBLICATIONS

International Search Report and Written Opinion dated Dec. 20, 2016 in PCT/US2016/056420.

(Continued)

*Primary Examiner* — Devin B Henson
(74) *Attorney, Agent, or Firm* — Oblon, McClelland, Maier & Neustadt, L.L.P.

(57) ABSTRACT

Described herein is an apparatus and method for generating a pain score for a patient. The method includes the steps of generating a PLR response signature for each drug of a plurality of drugs and further initiating a light stimulus to the patient, and measuring a corresponding PLR response. The method includes initiating a neuro-stimulus to the patient, the neuro-stimulus being initiated over a set of frequencies, each frequency being associated with a unique intensity, and stimulating a unique nerve fiber type of the patient, and measuring a PRD response of the patient for the initiated neuro-stimulus. Further, the method includes determining, for each nerve fiber type, a threshold response based on the measured PRD, determining a weight for each threshold response based on the PLR response, and combining the determined weight for each threshold response to obtain a pain score for the patient.

13 Claims, 20 Drawing Sheets

(51) Int. Cl.
    *A61B 3/11*     (2006.01)
    *A61B 5/11*     (2006.01)
    *A61B 3/00*     (2006.01)
    *A61B 3/14*     (2006.01)

(52) U.S. Cl.
    CPC .......... *A61B 5/1104* (2013.01); *A61B 5/1107* (2013.01); *A61B 5/4824* (2013.01); *A61B 3/145* (2013.01)

(56) References Cited

U.S. PATENT DOCUMENTS

| | | |
|---|---|---|
| 2012/0274906 A1 | 11/2012 | Privitera et al. |
| 2014/0063461 A1 | 3/2014 | Yao et al. |
| 2014/0268047 A1* | 9/2014 | Hirsh .................... A61B 3/112 351/206 |
| 2014/0276549 A1 | 9/2014 | Osorio |
| 2015/0116665 A1 | 4/2015 | Finkel |
| 2015/0245766 A1 | 9/2015 | Rennaker et al. |

OTHER PUBLICATIONS

Extended European Search Report dated May 20, 2019 in European Patent Application No. 16854564.8, 10 pages.
Chapman, C.R., et al., "Phasic pupil dilation response to noxious stimulation in normal volunteers: Relationship to brain evoked potentials and pain report", Psychophysiology, vol. 39, 1999, XP007919561, pp. 44-52.
Höfle, M., et al., "You can see pain in the eye: Pupillometry as an index of pain intensity under different luminance conditions", International Journal of Psychophysiology. vol. 70, 2008, XP025671083, pp. 171-175.
Ashe J.H., et al., "Multifiber Efferent Activity in Postganglionic Sympathetic and Parasympathetic Nerves Related to the Latency of Spontaneous and Evoked Pupillary Dilation", Experimental Neurology.
Supplementary Search Report dated Jun. 6, 2019, in European Patent Application No. 16854564.8-1115/3359015 PCT/US2016056420. (1 page).
Office Action dated Oct. 21, 2019 in China Patent Application No. 201680068044.5 (with English translation); 11 pgs.

\* cited by examiner

APPARATUS AND METHOD FOR PHYSIOLOGIC AND PHARMACODYNAMIC ASSESSMENT AND MONITORING

CROSS-REFERENCE TO RELATED APPLICATIONS

This application is based upon and claims the benefit of priority to provisional U.S. Application No. 62/284,787, filed Oct. 9, 2015, the entire contents of which are incorporated herein by reference.

BACKGROUND

Field of Disclosure

The present disclosure relates generally to an image capturing device that captures a video image of pupillary reflexes of an eye. The imaged pupillary reflexes include a pupillary light reflex (PLR), and a pupillary reflex dilation (PRD). Curves corresponding to the PLR and PRD are parametrized such that various dimensions of the reflexes can be determined. Moreover, relationships amongst the various dimensions are used to characterize and measure a particular condition or drug effect. The image-capturing device integrates a neuro-stimulator, and is able to produce the PRD, which can be used for analgesic monitoring and pain characterization.

Description of Related Art

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Healthcare providers are frequently faced with the problem of diagnosing and treating patients suffering from varying levels of pain. The appropriate assessment of a patient's pain is a prerequisite to successful diagnosis and treatment of the pain. However, healthcare providers often have difficulty in making such assessments due to patients' inability to accurately describe the pain that they are experiencing. Those difficulties sometimes result in ineffective, inadequate, and/or excessive treatments.

Traditionally, healthcare providers have used various apparatus/methods for subjectively, qualitatively, and/or semi-quantitatively measuring the amount and/or intensity of pain that a patient is suffering. The predominant apparatus/methods that have been used are categorical pain descriptors. Other methods that are typically used include pain tolerance threshold (PTT) and pain perception threshold (PPT).

A primary requirement for the success of such methods is that they rely on a patient's verbal response to indicate the level of pain. Thus, such methods cannot be used in patients who cannot convey the intensity or location of their pain to a physician or practitioner (e.g., patient's unable to comprehend their pain or a physician's queries, "non-verbal" patients or otherwise verbally or cognitively challenged patients, patients with developmental disabilities, etc.).

Accordingly, there is a requirement for an apparatus and method for objectively and quantitatively assessing and characterizing pain in all types of patients.

SUMMARY

An aspect of the present disclosure provides for a method for generating a pain score for a patient. The method includes the steps of generating a PLR response signature for each drug of a plurality of drugs; initiating a light stimulus to the patient, and measuring a corresponding PLR response; initiating a neuro-stimulus to the patient, the neuro-stimulus being initiated over a set of frequencies, each frequency being associated with a unique intensity, and stimulating a unique nerve fiber type of the patient; measuring a PRD response of the patient for the initiated neuro-stimulus; determining, for each nerve fiber type, a threshold response based on the measured PRD; determining a weight for each threshold response based on the PLR response; and combining the determined weight for each threshold response to obtain a pain score for the patient.

One aspect of the present disclosure provides for an apparatus that includes circuitry configured to generate a PLR response signature for each drug of a plurality of drugs; initiate a light stimulus to the patient, and measuring a corresponding PLR response; initiate a neuro-stimulus to the patient, the neuro-stimulus being initiated over a set of frequencies, each frequency being associated with a unique intensity, and stimulating a unique nerve fiber type of the patient; measure a PRD response of the patient for the initiated neuro-stimulus; determine, for each nerve fiber type, a threshold response based on the measured PRD; determine a weight for each threshold response based on the PLR response; and combine the determined weight for each threshold response to obtain a pain score for the patient.

An aspect of the present disclosure provides for a non-transitory computer readable medium including computer executed instructions that when executed by a computer, cause the computer to execute a method for generating a pain score for a patient. The method includes the steps of generating a PLR response signature for each drug of a plurality of drugs; initiating a light stimulus to the patient, and measuring a corresponding PLR response; initiating a neuro-stimulus to the patient, the neuro-stimulus being initiated over a set of frequencies, each frequency being associated with a unique intensity, and stimulating a unique nerve fiber type of the patient; measuring a PRD response of the patient for the initiated neuro-stimulus; determining, for each nerve fiber type, a threshold response based on the measured PRD; determining a weight for each threshold response based on the PLR response; and combining the determined weight for each threshold response to obtain a pain score for the patient.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

Various embodiments of this disclosure that are proposed as examples will be described in detail with reference to the following figures, wherein like numerals reference like elements, and wherein.

DETAILED DESCRIPTION OF EMBODIMENTS

Figure 1:
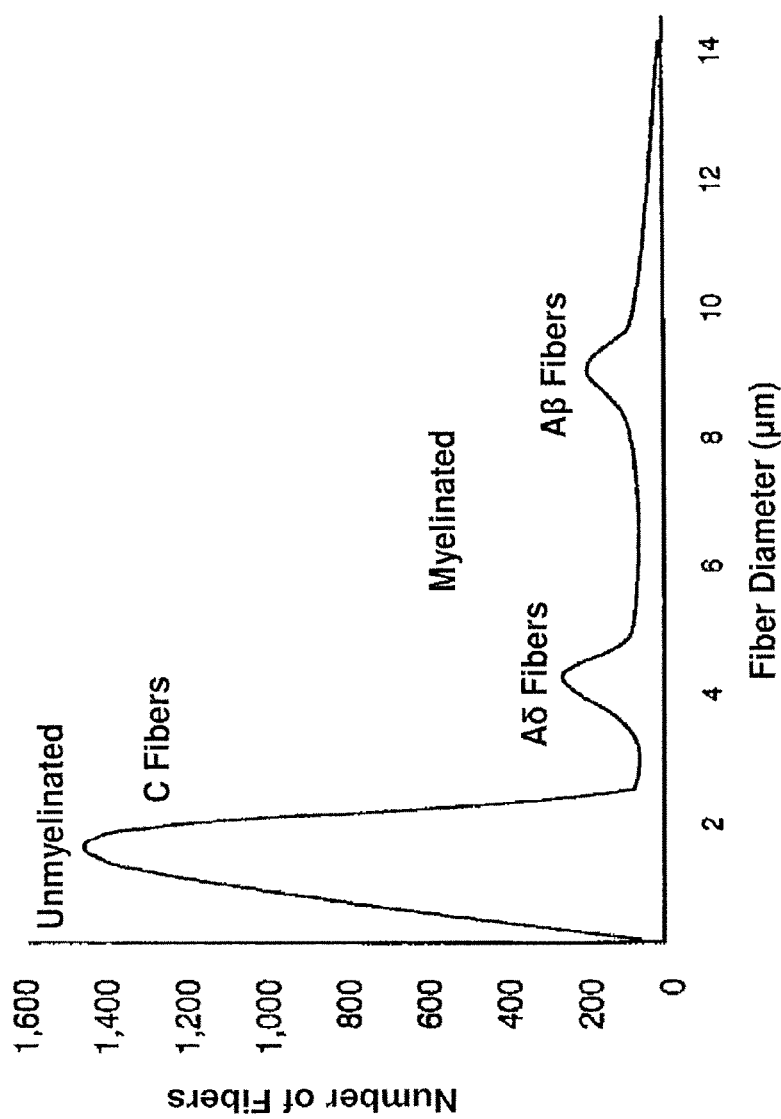
FIG. 1 depicts according to an embodiment, a graph illustrating nerve-fiber-diameter distribution of a human sensory nerve, and a chart listing neuro-specific electrical stimulation for those nerve fibers.

Exemplary embodiments are illustrated in the referenced figures of the drawings. It is intended that the embodiments and figures disclosed herein are to be considered illustrative rather than restrictive. No limitation on the scope of the technology and of the claims that follow is to be imputed to the examples shown in the drawings and discussed herein.

The embodiments are mainly described in terms of particular processes and systems provided in particular implementations. However, the processes and systems will operate effectively in other implementations. Phrases such as "an embodiment", "one embodiment" and "another embodiment" may refer to the same or different embodiments. The embodiments will be described with respect to methods and compositions having certain components. However, the methods and compositions may include more or less components than those shown, and variations in the arrangement and type of the components may be made without departing from the scope of the present disclosure.

The exemplary embodiments are described in the context of methods having certain steps. However, the methods and compositions operate effectively with additional steps and steps in different orders that are not inconsistent with the exemplary embodiments. Thus, the present disclosure is not intended to be limited to the embodiments shown, but is to be accorded the widest scope consistent with the principles and features described herein and as limited only by the appended claims.

Furthermore, where a range of values is provided, it is to be understood that each intervening value between an upper and lower limit of the range—and any other stated or intervening value in that stated range is encompassed within the disclosure. Where the stated range includes upper and lower limits, ranges excluding either of those limits are also included. Unless expressly stated, the terms used herein are intended to have the plain and ordinary meaning as understood by those of ordinary skill in the art. The following definitions are intended to aid the reader in understanding the present disclosure, but are not intended to vary or otherwise limit the meaning of such terms unless specifically indicated.

Aspects of the present disclosure provide for an image capturing apparatus that is configured to capture a video image of pupillary reflexes of the eye. The imaged reflexes are of two types: a first reflex, referred to herein as a pupillary-light-reflex (PLR), and a second reflex referred to herein as a pupillary-reflex-dilation (PRD). By one embodiment, the PLR and the PRD reflex curves are parametrized, such that various dimensions of the PLR and PRD reflexes can be determined, and relationships amongst the various dimensions can be analyzed. Such an analysis provisions for the characterization and measurement (and/or monitoring) of a particular condition or drug effect. Moreover, the apparatus includes a neuro-stimulator that is enabled to produce and process the PRD curve, and further utilize the PRD for analgesic monitoring and pain characterization.

By one embodiment, the neuro-stimulator can be integrated with a smartphone device, or may be a standalone device, referred to herein as an 'infrared-pupilometer'. Such a device provides at least, the following advantageous abilities: objective, qualitative, and quantitative measurement of pain, determination of sensory detection thresholds (SDTs), analgesic effects of drugs and other pain interventions, pharmacodynamic impact of analgesics and other pain interventions, the efficacy and dose-response relationships of investigational drugs and other interventions targeted for the management of pain, and the onset of tolerance and/or analgesic-induced toxicity from different drugs and pain interventions.

Furthermore, techniques of the embodiments described herein also provide for the objective characterization of different pain or sensory conditions (e.g., neuropathic pain, hyperalgesia, allodynia, depression, anxiety etc.). Specifically, neuro-specific electrical stimulation can be applied to a patient incrementally until it causes activation of specific sensory nerve fibers (i.e., until a threshold action potential is generated at the targeted nerve fiber), but without inciting the emotional component of pain. In other words, sensory nerve fibers can be activated up to the point where sensation is detected without overt pain, and without any bodily harm.

Moreover, as the patient does not incur overt pain, PRD can be used to measure a level of nociception (defined herein as a neural process of encoding noxious stimuli), experienced by the patient. As aspect of the present disclosure provides for a technique of integrating PLR and PRD responses to provide a direct correlation of a measured level of nociception experienced by the patient with the type of neuro-specific electrical stimulation being applied. Thus, an objective, qualitative, and quantitative measurement of the patient's response to that stimulation can be obtained. Note that the IR video pupilometer component of the device can measure both pupillary reflexes; the pupillary light reflex (PLR) and the PDR. Depending on the condition being examined, (e.g., opioid induced tolerance) indices relating the two reflexes are used to describe the condition and provide decision support.

By one embodiment, the patient's measured response to the neuro-specific electrical stimulation is used to determine the patient's SDT and to provide a diagnostic characterization of the patient's stimulus response (e.g., neuropathic pain, hyperalgesia, allodynia, etc.). The measured response can also be used to determine the analgesic impact of different drugs and pain interventions on the patient's SDT, depending on the type of neuro-specific electrical stimulation that is applied. By one embodiment, by repeating the measurements over a period of time, one can detect the onset of tolerance and/or analgesic-induced toxicity from different drugs. Thus, aspects of the present disclosure not only provide for an apparatus and method for objectively and quantitatively assessing pain in patients, they also provide an apparatus and method for objectively measuring the analgesic effect drugs and other pain interventions, measuring the efficacy and dose-response relationships of investigational drugs and other interventions targeted for the management of pain.

To that end, advantages provided by the above described aspects of the present disclosure can be better understood from the description of the preferred embodiments below and the accompanying drawings. In describing the preferred embodiments, specific terminology is resorted to for the sake of clarity. However, the present disclosure is not intended to be limited to the specific terminology so selected, and it must be appreciated that each specific term includes all technical equivalents that operate in a similar fashion to accomplish a similar purpose. For instance with regard to the different types of fibers as described next with reference to FIG. 1, the terms 'Aβ fiber', 'Aδ fiber', and 'C-fiber' are used not only to refer specifically to the primary nerve fibers in human skin, but rather, they are used more generally to refer to the corresponding nerve fibers in muscles, joints, and viscera (e.g., Group II, III, and IV nerve fibers).

The somatosensory system comprises receptors and processing centers that produce sensory modalities such as touch, temperature, body position, and pain. Sensory receptors are nerve endings that cover the skin and epithelia, skeletal muscles, bones and joints, and viscera of the human body. The sensory receptors are innervated by different types of nerve fibers, and initiate sensory transduction in response to stimuli by creating graded potentials or action potentials in the same cell or in an adjacent cell. The nerve fibers can be classified based on such characteristics as axonal conduction velocity, refractory period, fiber size, and myelination (i.e., production of a myelin sheath surrounding the axon of a nerve cell).

Turning to FIG. 1, there is provided a graph illustrating the nerve-fiber-diameter distribution of a human sensory nerve, and a chart listing corresponding nerve fiber characteristics. A typical human sensory nerve comprises primary afferent fibers bundled together. The primary fibers in human skin include large-diameter (e.g., 5-12 µm) myelinated A-beta (Aβ) fibers, medium-diameter (i.e., 2-5 µm) myelinated A-delta (Aδ) fibers, and small-diameter (i.e., 0.2-1.5 µm) unmyelinated C-fibers.

The primary fibers in human muscles are subdivided into analogous groups of myelinated axons—Group II fibers, which are analogous to Aβ fibers, Group III fibers, which are analogous to Aδ fibers, and Group IV fibers, which are analogous to C-fibers. The primary fibers in joints include Groups II, III, and IV fibers as well as Group I fibers, the latter of which do not have analogous skin fibers, but are similar to Aδ muscle fibers. Each of these major fiber types has its own characteristic neurophysiological profile, sensory function, depolarization characteristics and sensation evoked by electrical stimulation, and conduction block susceptibility.

For example, Aβ fibers are linked with various cutaneous mechanoreceptors and a small number of visceral mechanoreceptors, and Group I and II fibers are linked with muscle mechanoreceptors and joint mechanoreceptors. Aβ and Group I and II fibers are considered "low threshold" fibers because they detect non-noxious stimuli to the skin (e.g., skin indentation, skin and hair movement, vibration of the skin and hair, etc.), muscles (e.g., changes in muscle length, muscle tension, muscle contraction, vibration of the muscle, etc.), and joints (e.g., distension of the joint, contraction of the joint, vibration of the joint, etc.). Aβ and Group II fibers have a quick conduction velocity (e.g., 30-75 m/s and 24-71 m/s, respectively), with Group I fibers having an even quicker conduction velocity (e.g., 72-120 m/s). Aβ and Group II fibers typically conduct impulses that signal the perception of touch, pressure, and/or vibration. Conduction of such signals is most susceptible to blockage by applying compression to the affected area.

Aδ, C, and Group III and IV fibers are linked with mechanoreceptors, thermoreceptors, and poly-modal nociceptors. These fibers are considered "high threshold" fibers because they detect a higher intensity of stimulation (i.e., noxious stimulation) than Aβ and Group I and II fibers (i.e., non-noxious stimulation). They detect noxious stimulation to the skin (e.g., intense pressure, severe temperatures, damage to skin tissue, etc.), muscles (e.g., intense pressure, ischemia, damage to muscle tissue, etc.), and joints (e.g., extreme bending, innocuous movement, probing of the joint, etc.). Some of those fibers do not differentiate noxious from non-noxious stimuli, while others respond only to painfully intense stimuli.

Aδ and Group III fibers have an intermediate conduction velocity (e.g., 12-30 m/s and 6-23 m/s, respectively), while C and Group IV fibers have a slow conduction velocity (e.g., 0.3-1.5 m/s and <2.5 m/s, respectively). Part of the difference in conduction velocity between Aδ and Group III fibers, and C and Group IV fibers is attributed to the fact that Aδ and Group III fibers are myelinated (i.e., they are thinly sheathed in myelin, which is an electrically insulating material), while C and Group IV fibers are not. Accordingly, stimulation of Aδ and Group III fibers elicits an early, rapid pain that is sharp in nature, while stimulation of C and Group IV fibers elicits a later, prolonged pain that is dull and achy in nature.

In other words, Aδ and Group III fibers typically conduct impulses that signal the initial perception of pain from extreme pressure, severe temperature, and/or injury, while C and Group IV fibers conduct impulses that signal a prolonged aching experience following the initial perception of pain. Conduction of signals by Aδ and Group III fibers is most susceptible to blockage by depriving the affected area of adequate oxygen supply, and conduction of signals by C and Group IV fibers is most susceptible to blockage by anesthetizing the affected area.

Returning to FIG. 1, unmyelinated C fibers are the most prevalent fibers in a typical human sensory nerve (~80%), with Aδ and Aβ fibers being equally less prevalent with one another (~10% each). The small-diameter C fibers have the longest refractory period, with the larger diameter Aδ and Aβ fibers having shorter refractory periods. The differences in those refractory periods are presumably a direct result of the quantity of ion channels available per surface area of each fiber. Smaller diameters also yield higher charge thresholds and require a longer duration of stimulus depolarization to generate an action potential at the fiber. For example, in the absence of pharmacologic interventions or pathologic conditions, a range of sine waves from 0.01-2.0 mA can be applied to C-fibers at a frequency of 5 Hz to generate action potentials at those fibers. A range of sine waves from 0.03 to 2.2 mA can be applied to Aδ fibers at a frequency of 250 Hz to generate action potentials at those fibers, and a range of sine waves from 0.22 to 6.0 mA can be applied to Aβ fibers at a frequency of 2,000 Hz to generate action potentials at those fibers. A sine wave is preferably used because of that waveform's frequency-dependent rate of depolarization.

Because smaller diameters yield longer refractory periods, the sine wave stimulus can be applied for different periods of time so as only to affect a specific nerve fiber. For example, the Aβ fibers can respond to a short duration (e.g., ~0.25 ms) of sine wave stimulation applied at a frequency of 2,000 Hz while the smaller-diameter fibers (i.e., Aδ and C fibers) require a significantly longer period (e.g., ~100 ms for a C fiber) of sine wave stimulation to respond. The Aβ fibers will re-polarize more quickly than the frequencies (e.g., 5 Hz and 250 Hz) used to generate an action potential in the smaller-diameter fibers (i.e., Aδ and C fibers) can depolarize the Aβ fibers.

In other words, smaller-diameter fibers do not achieve their threshold action potentials over shorter durations, and larger-diameter fibers do not achieve their threshold action potentials at lower frequencies. Together those factors allow selective responses to be separately evoked from Aβ, Aδ, and C fibers using different frequencies (Hz), intensities (mA), and durations (ms) of electrical stimulation. Accordingly, the type of targeted electrical stimulation is hereinafter referred to as "neuro-specific" electrical stimulation, and the device that allows a user to select between those targets is hereinafter referred to as "neuro-selective" stimulator. The neuro-selective stimulator is described later with reference to FIG. 13B.

Figure 2:
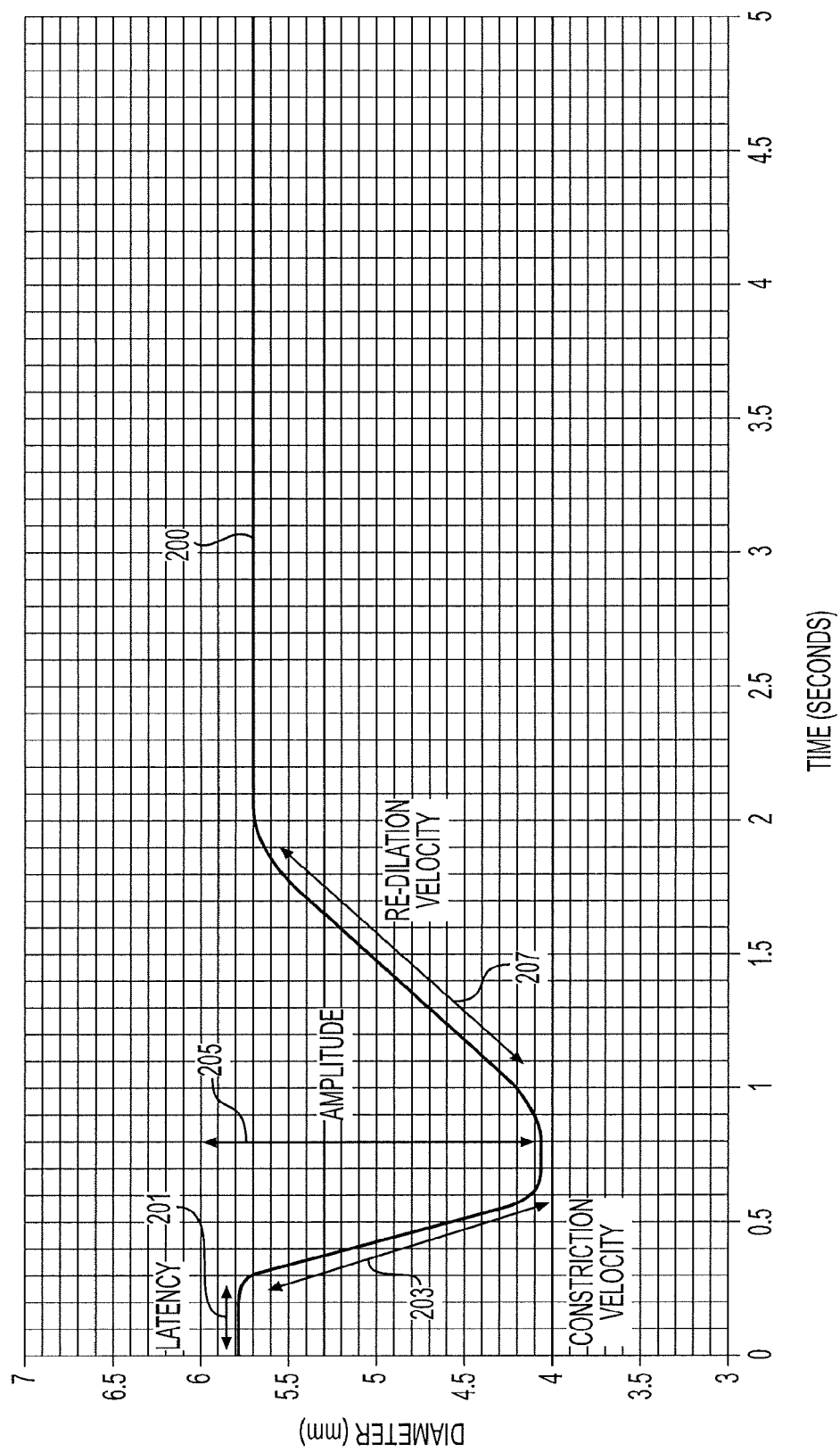
FIG. 2 depicts an exemplary graphical representation of parameters of a pupillary light reflex curve (PLR)

FIG. 2 depicts an exemplary graphical representation of parameters of a pupillary light reflex curve (PLR). By one embodiment, a transient flash of light produces a decrease in pupil size. The reflex can be described by variables such as light reflex amplitude, latency of the light reflex, constriction velocity (CV), and dilatation velocity (DV). As there is significant correlation among the measured variables, reflex amplitude can be measured and utilized to describe the light reflex. Examination of PLR is a mandatory portion of a physical examination. Evaluation of the light reflex with an infrared pupilometer is noninvasive, easily tolerated by patients, and takes only a few seconds.

As shown in FIG. 2, the PLR curve 200 includes a portion 201 that corresponds to the parameter latency, a portion 203 (i.e., a descending portion of the curve 200) that corresponds to constriction velocity, a portion 205 which corresponds to amplitude, and a portion 207 (i.e., an ascending portion of the curve 200), which corresponds to re-dilation velocity. Note that different drugs and disease-processes may impact the curve 200 in characteristic ways, thus allowing for one to ascribe a 'signature' to a drug or process.

Moreover, in order to differentiate between curve responses based on the type of medication/drug, by one embodiment, Fourier transform operations, or dynamic-time-warping algorithms can be implemented to provide comprehensive analysis of the curves to generate the signatures. Additionally, techniques including cross-correlation and root-mean-square deviation analysis can be implemented with curve shape features, such as local curvature and shape index, and measures of smoothness and jaggedness.

As defined previously, nociception is the neural process of encoding noxious (painful) stimuli. PRD is one of the autonomic responses that results from encoding a noxious stimulus and can be measured using an infrared pupilometer. An alerting stimulus in awake subjects dilates the pupil primarily by activating the sympathetic radial muscle. PRD is activated by diverse stimuli such as loud sounds or nociceptive stimuli. Because a noxious stimulus of minimal intensity will evoke PRD, the PRD reflex can be used to detect potentially painful sensations in non-communicating patients. The pupillary dilation and increase in the light reflex during painful stimuli can be used as objective measures of nociception in patients who are awake but unable to communicate pain levels.

By one embodiment of the present disclosure, there is provided an apparatus referred to herein as a pupil-algometer. The pupil-algometer measures pain intensity, pain type, and analgesic suitability. Further, the pupil-algometer is able to measure pain sensitivity and intensity, and pain type by imaging the pupillary reflex dilation (PRD) while a painful or potentially painful stimulus occurs. Moreover, the pupil-algometer enables identification of a type of pain i.e., neuropathic or nociceptive, via interpretation of parametrized graphs of the PRD and PLR. In addition to determining the type of pain, the suitability of a particular analgesic drug class can also be determined and the device can monitor dose response relationships.

By one embodiment, the pupil-algometer integrates a neuro-specific neuro-stimulator with a smartphone device. The neuro-stimulator depolarizes specific sensory nerve fiber types in response to a particular frequency. For instance, as stated previously, frequencies of 2000 Hz, 250 Hz, and 5 Hz can be used to query Aβ (touch), Aδ (sharp lancinating pain), and C (slow burning pain) fibers, respectively. The stimulus can be provided through a small probe placed on a finger for systemic evaluations or upon an area of concern at variable intensities ranging from a perception threshold to a tolerance threshold. However, it is preferable to use stimuli whose magnitude is less than 9 milliamps (mA) (as such a stimulus does not cause injury). The thresholds responses in the PRD yield tremendous diagnostic information. For instance, low threshold responses in the Aβ nerve indicate the presence of neuropathic pain. An increase in the threshold with the use of gabapentin would thus indicate clinical effectiveness. Moreover, dose escalation can be attempted and evaluated to determine if there is increasing efficacy.

Figure 3A:
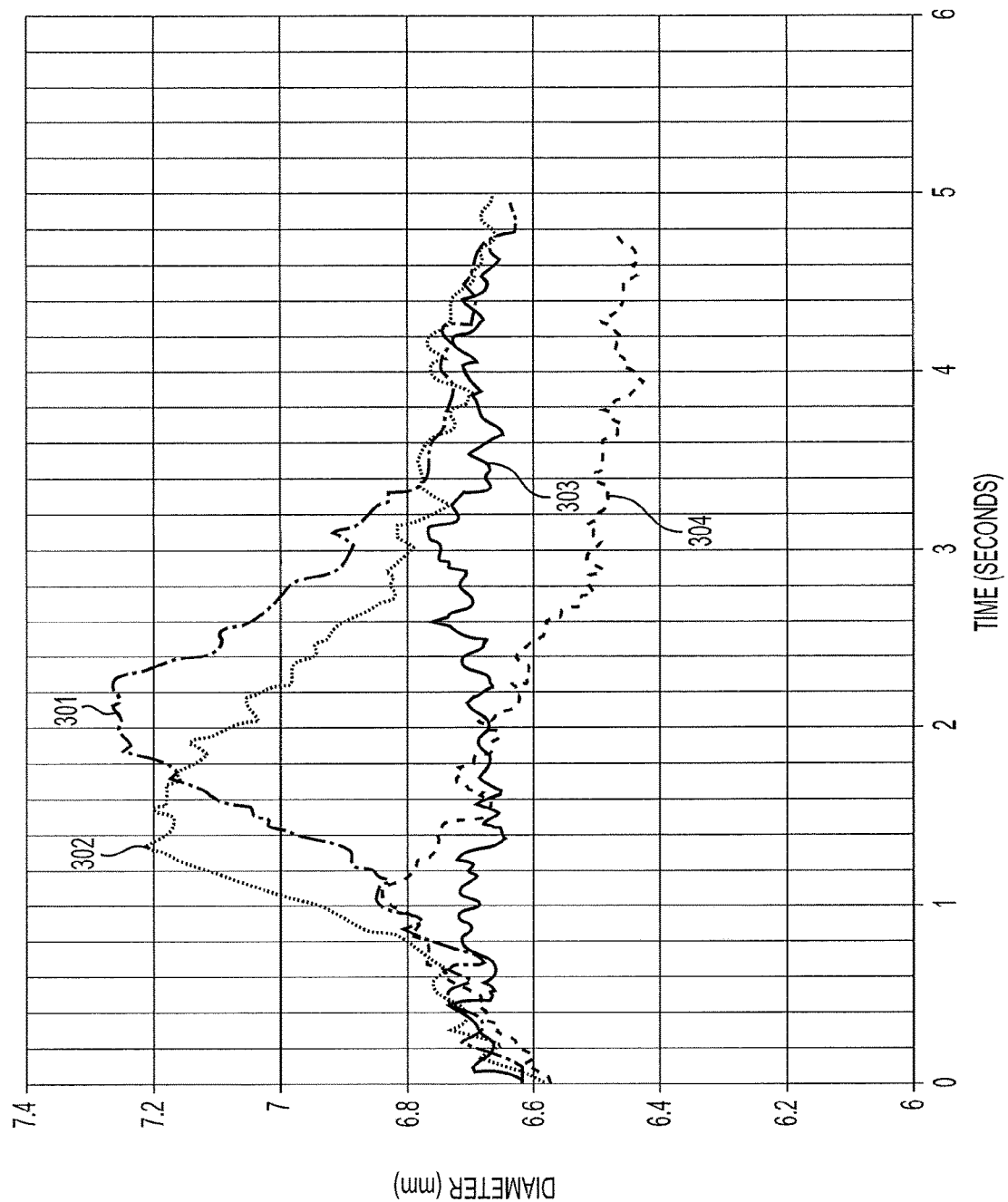
FIGS. 3A-3C depict exemplary pupillary reflex dilation (PRD) curves for Aβ-fiber, Aδ-fiber, and C-fiber, respectively.

FIG. 3A depicts an exemplary PRD curve corresponding to the Aδ-fiber. The PRD intensity-response relationship is generated by utilizing a 250 Hz signal. The graph in FIG. 3A corresponds to a 1 second of stimulation followed by the PRD. Referring to FIG. 3A, curve 301 corresponds to a signal of magnitude 9 mA, curve 302 corresponds to a signal of magnitude 7 mA, and curve 304 corresponds to a signal of magnitude 5 mA, whereas the curve 303 corresponds to no stimulus being applied.

Figure 3B:
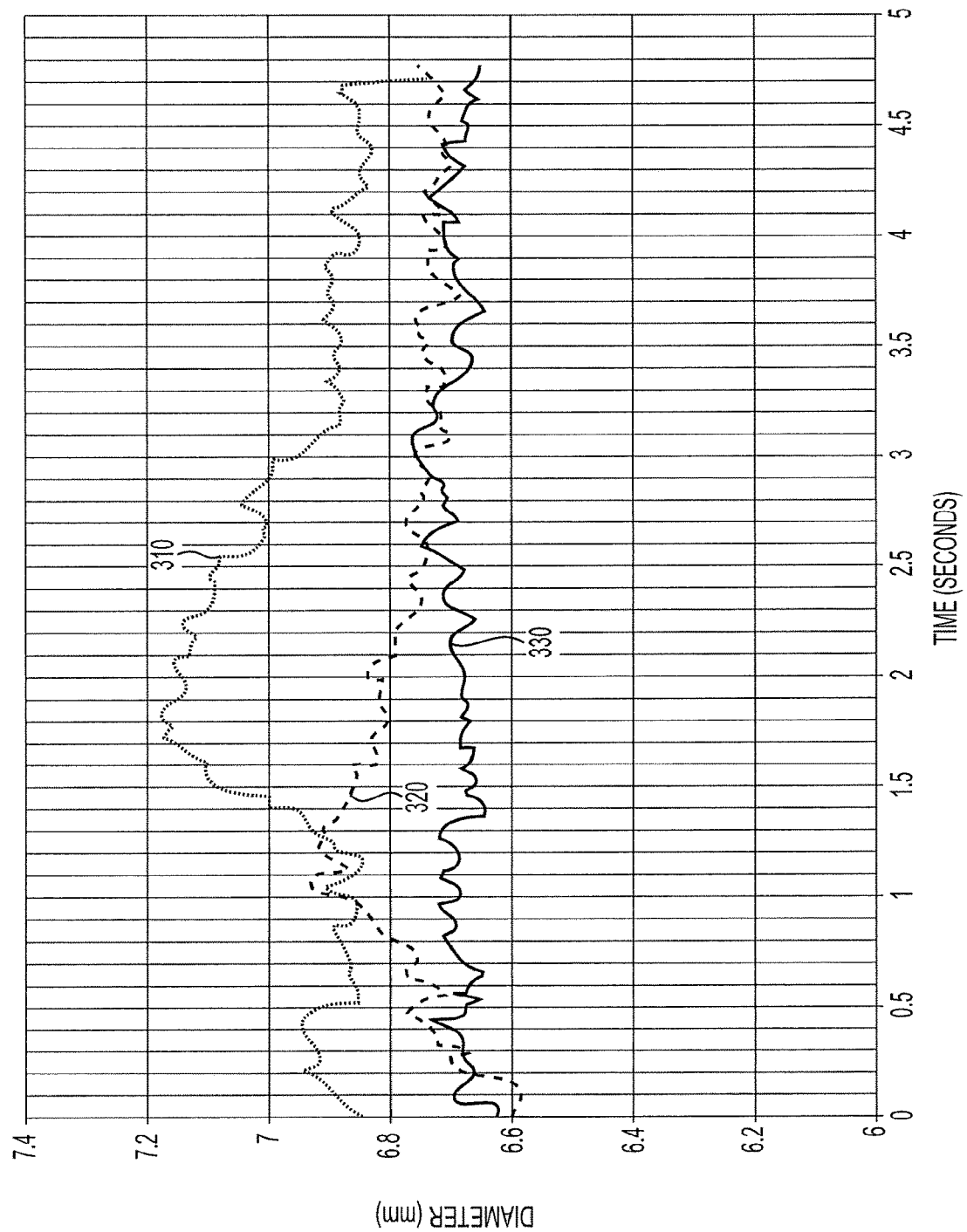

FIG. 3B depicts an exemplary PRD curve corresponding to the Aβ-fiber. The PRD intensity-response relationship is generated by utilizing a 2000 Hz signal. The graph in FIG. 3B corresponds to a one second of stimulation, followed by the PRD. Referring to FIG. 3B, curve 310 corresponds to a signal of magnitude 9 mA, curve 320 corresponds to a signal of magnitude 5 mA, and curve 330 corresponds to no stimulus being applied. Note that the Aβ nerve is normally not a pain fiber, but rather transmits neuropathic pain. The PRDs (FIG. 3B) are thus flatter in normal subjects. At high intensities, Aδ nerves are recruited, thereby accounting for the peak amplitude in the 9 mA curve. Thus, a patient with neuropathic pain would have high amplitudes in response to low intensity stimulation.

Figure 3C:
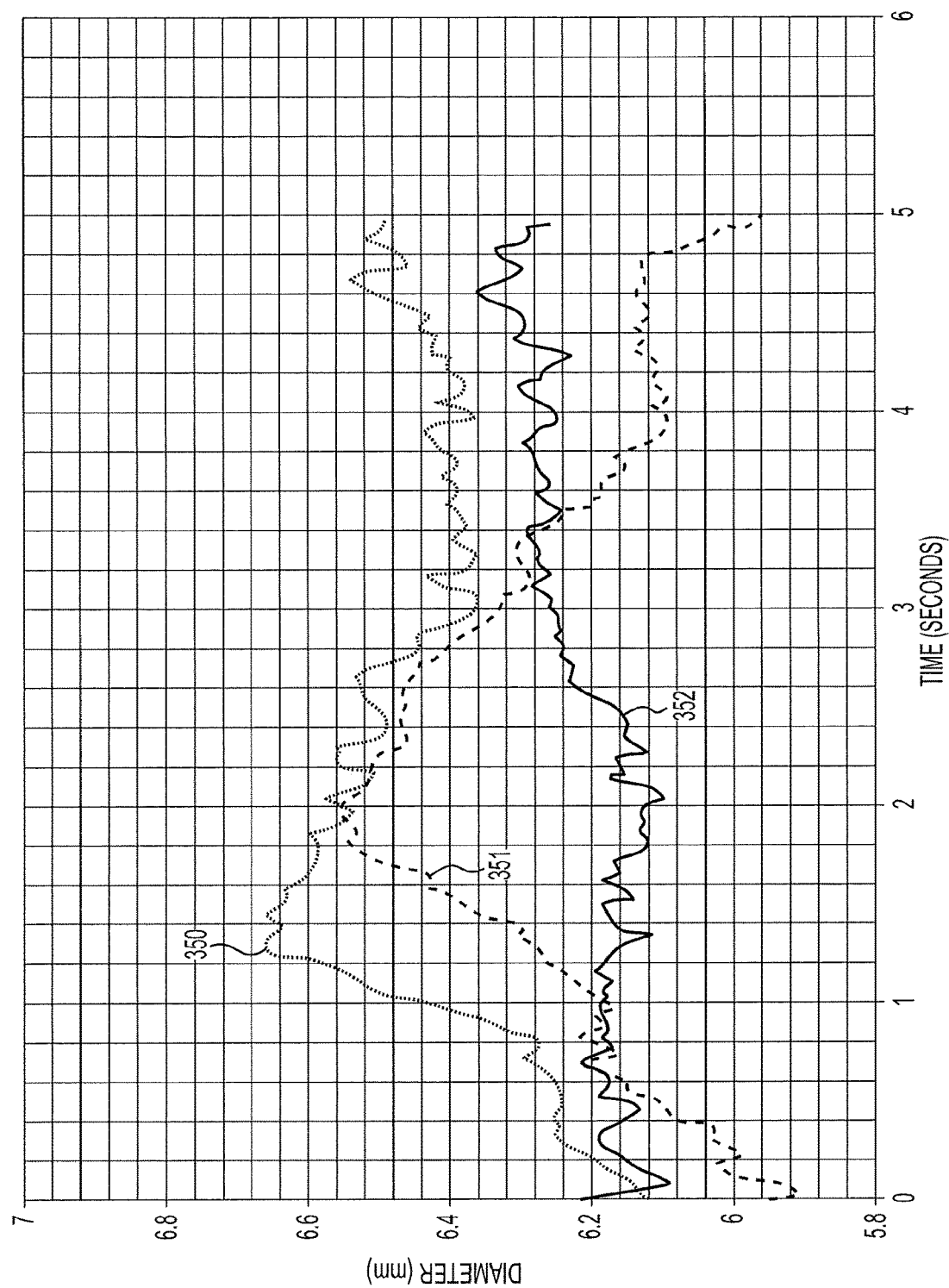

FIG. 3C depicts an exemplary PRD curve corresponding to the C-fiber. The PRD intensity-response relationship is generated by utilizing a 5 Hz signal. The graph in FIG. 3C corresponds to a 1 second of stimulation followed by the PRD. Referring to FIG. 3C, curve 350 corresponds to a signal of magnitude 9 mA, curve 351 corresponds to a signal of magnitude 5 mA, and curve 352 corresponds to no stimulus being applied. It must be appreciated that the C-fiber transmits slow burning pain and is populated by opioid receptors. Thus, the PRDs are diminished after a dose of opioid for a given intensity stimulus.

Figure 4:
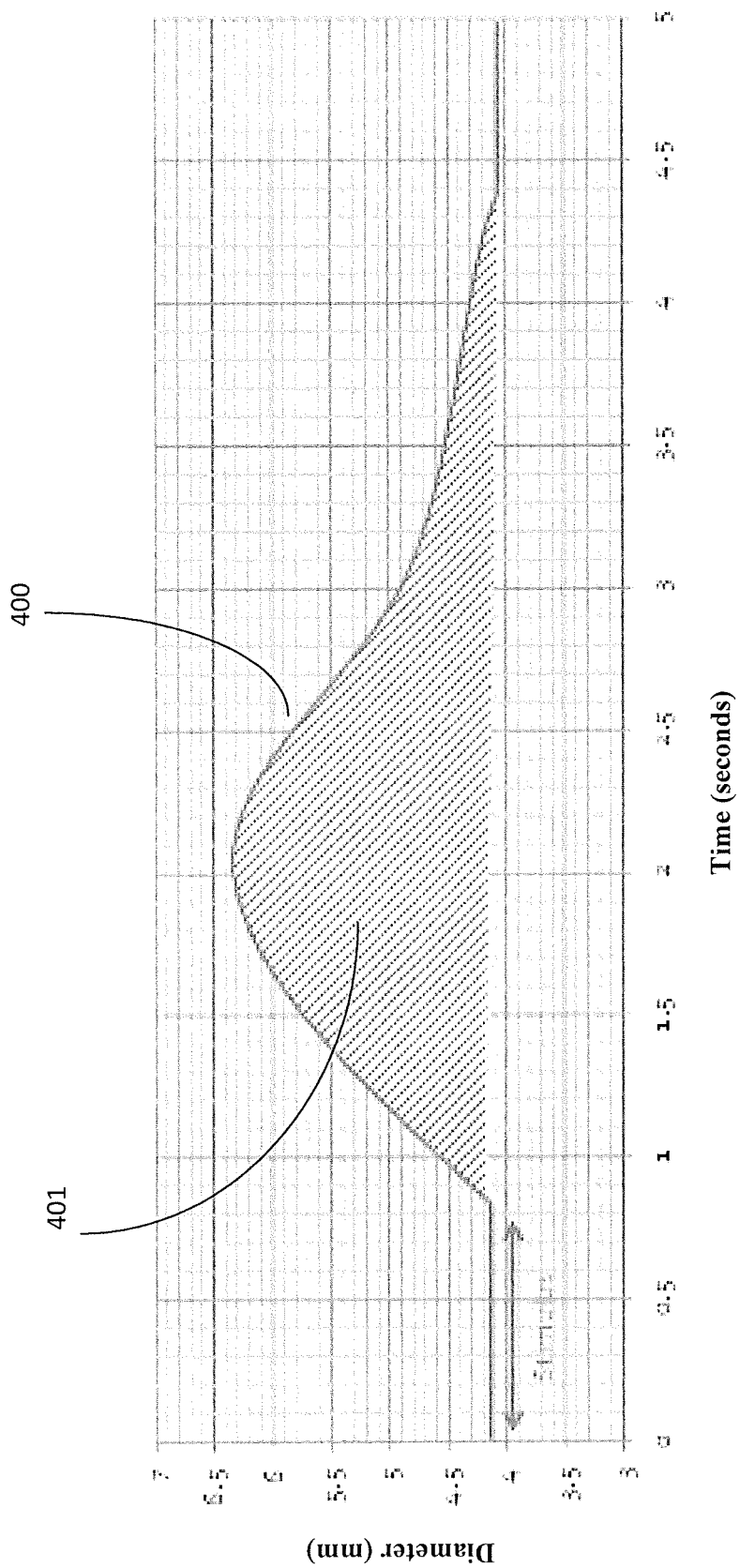
FIG. 4 depicts an exemplary graphical representation of a monophasic non-noxious neuro-specific stimulus induced PRD.

According to one embodiment of the present disclosure, a PRD can be produced using a sub-threshold (i.e., perception only) neuro-specific electrical stimulus. FIG. 4 depicts an exemplary graphical representation of a monophasic non-noxious neuro-specific stimulus induced PRD. In FIG. 4, the shaded area 401 under the curve 400 indicates pain sensitivity. The non-noxious technique of administering the neuro-stimulus is that a substantially pain-free experience is provided for the patient.

Figure 5:
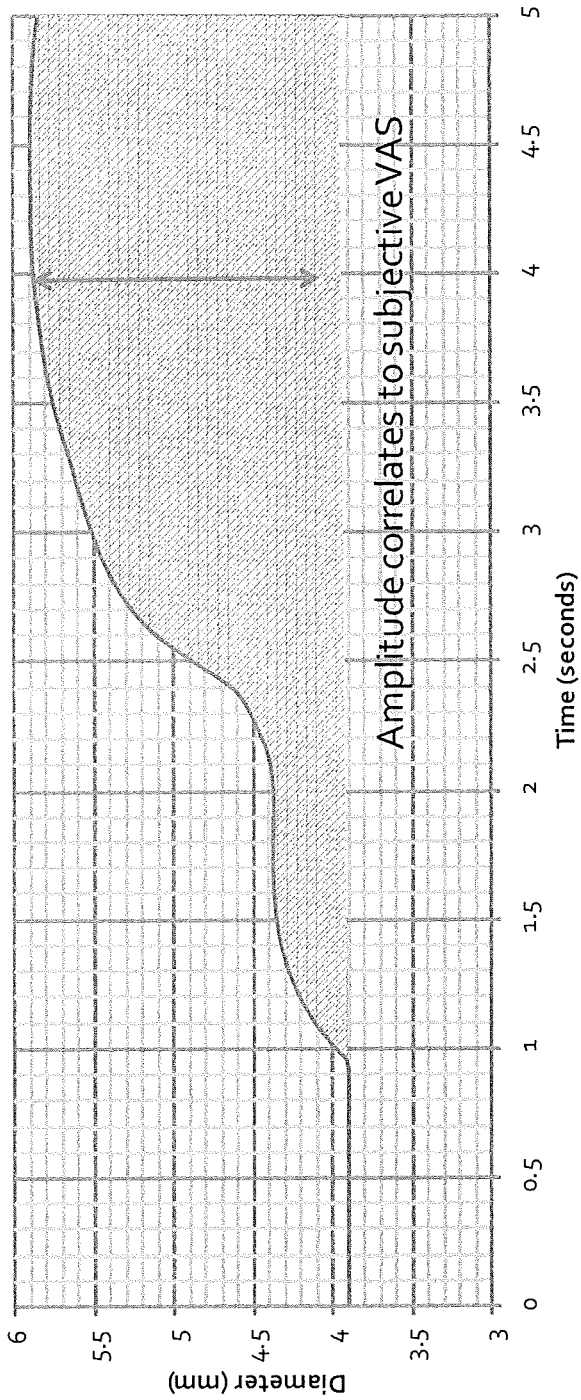
FIG. 5 depicts a clinical PRD obtained in response to a painful stimulus.

In contrast, FIG. 5 depicts a 'clinical' PRD obtained in response to a painful clinical or traumatic stimulus. The PRD as depicted in FIG. 5 is biphasic in nature and is obtained in response to a clinical pain stimulus such as a manipulation of a broken bone. By one embodiment, data from both these reflexes (FIG. 4 and FIG. 5) can be captured and processed to render a digital or descriptive output from the pupil-algometer by applying analyses such as the Fourier Transform. The resulting coefficients can be used to identify the relative contribution of specific parameters to identify a given drug, drug-drug interaction or physiologic characteristic such as pain type, intensity, concussion or dysautonomia.

According to one embodiment, the neuro-stimulator can be integrated with a smartphone, thereby allowing for the detection of mechanism specific nociception via recording and parameterization of the PRD under a multitude of conditions. Parameterization of the PRD curve includes two static measures: a pupillary baseline and peak dilation diameters (dilation amplitude or DA), and at least three dynamic measures: slopes of the ascending and descending portions of the PRD curve representing the dilation velocity (DV) and recovery velocity, as well as the duration of the reflex, and the area under the curve representing pain sensitivity/intensity.

The use of neuro-specific stimulation allows for the objective discrimination between nociceptive and neuropathic pain. This is an important distinction when choosing a therapeutic intervention. Nociceptive pain signals are transmitted via Aδ and C nerve fiber types that are stimulated at 250 Hz and 5 Hz, respectively. Neuropathic pain is transmitted via Aβ nerve fiber type, which is stimulated at 2000 Hz. Suitability for particular analgesics can thus be determined via PRD threshold testing. For instance, an example testing paradigm would be a 1 second stimulus duration at a predetermine intensity for the 250 and 2000 Hz frequencies, and a 2 second duration for the 5 Hz frequency that are to be performed in order of 5 Hz, 250 Hz and 2000 Hz, with a minute interval between frequencies. It must be appreciated that the testing paradigm is not limited to this example, and can be varied depending on the query being investigated. The SDT is determined in a verbal patient by administering a stimulus of increasing intensity until the subject no longer wants to feel the next intensity stimulus. As shown previously in FIGS. 3A-3C, for non-verbal patients, the SDT is maintained in the non-aversive range, generally below 5 mA, depending on the query. For clinical evaluation of anti-nociceptive intervention, a single low intensity stimulus (e.g., 2 mA) that would represent perception threshold is adequate.

It must be appreciated that different classes of analgesics will impact specific fiber types, and therefore specific types of pain. By one embodiment of the present disclosure is provided a technique of identifying a type of pain, which allows for the appropriate selection of an analgesic, and further provides an objective monitoring tool via serial measures. For instance, opioids modulate nociceptive pain. Specifically, the mu-opioid receptor populates C-fibers, and thus opioids will selectively impact the 5 Hz PRD parameters. Moreover, a dose ranging effect can also be determined via monitoring with the PRD by giving incremental doses in order to decrease the amplitude of a given intensity stimulus to a desired amplitude (e.g., 50% reduction).

By one embodiment of the present disclosure is provided a method for assessment of all aspects of opioid analgesia. With regard to opioids, specific parameters of the PLR, such as a resting pupil size parameter, and CV are inversely related to opioid dose with acute administration. With chronic administration, the impact on static measures of pupil size and CV reverses, thereby allowing for the identification of tolerance. When the impact on these parameters actually increases from base-line, it is indicative of opioid induced hyperalgesia, a neuro-excitatory condition.

In the present embodiment, diagnostic ability is enhanced by introducing a neuro-specific impact on the PRD. The mu-opioid receptors populate the C-fiber, which are depolarized by a 5 Hz stimulus. The presence of an opioid will increase the threshold (intensity stimulus) for a given amplitude response. It follows that the amplitude response to opioid tolerance would be greater or a greater dose would be necessary to achieve the same diminution originally achieved. Furthermore, opioid induced hyperalgesia would be represented by an increase in pain sensitivity reflected by an increased amplitude response to a specified intensity stimulus. Accordingly, a score (i.e., an index), for instance, in this case, an 'opioid tolerance index' indicating the degree of opioid tolerance is established using the relationship of the noted parameters of the PLR to parameters of the PRD including, but not limited to, the maximum dilation velocity (MDV), the area under the curve (AUC) and the recovery time to baseline (RT). In this manner, a monitoring tool that observes chronic use of the drug class is obtained.

Figure 6:
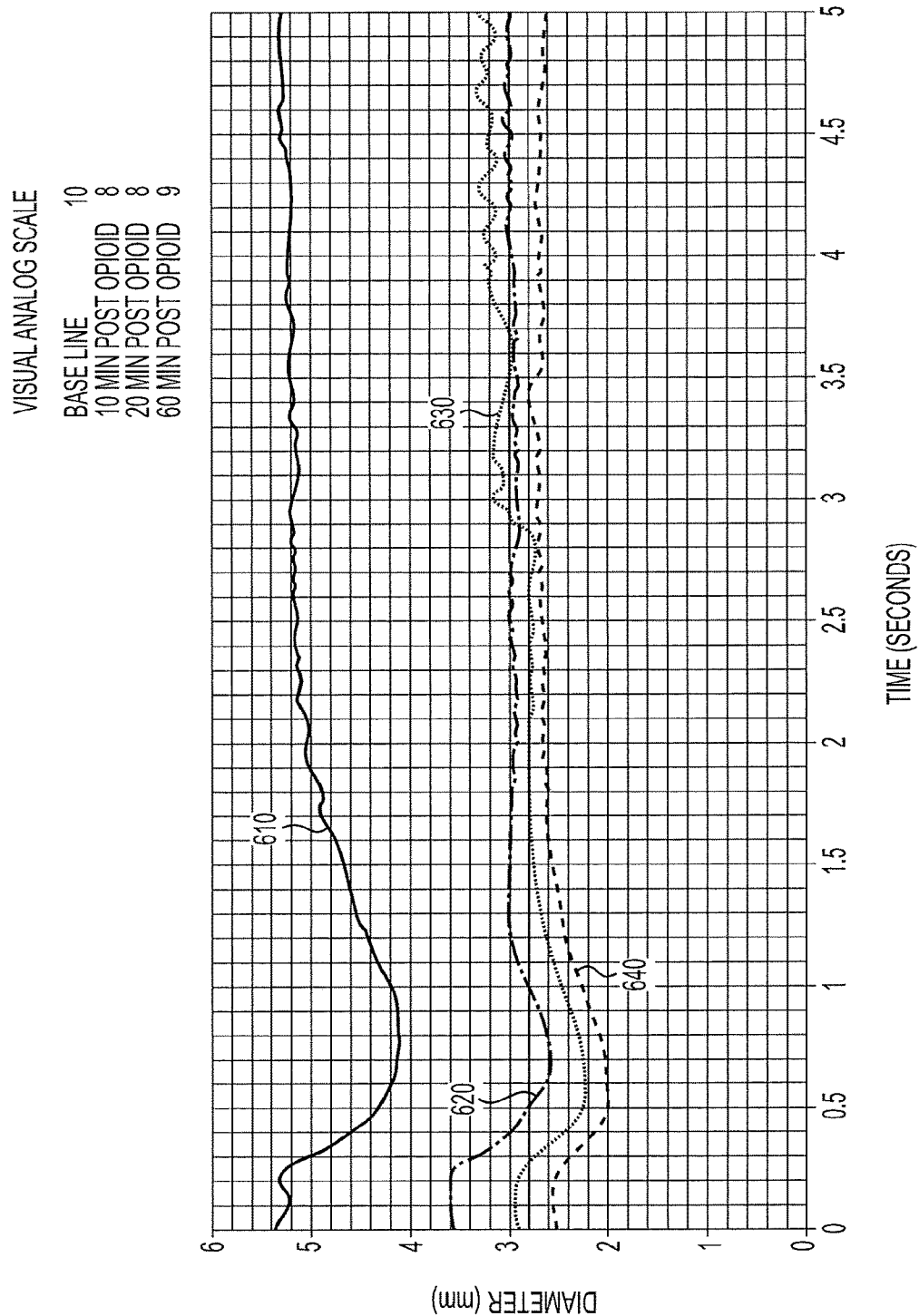
FIG. 6 depicts an exemplary graphical representation of the PLR response to a single bolus dose of hydromorphone.

Turning to FIG. 6, there is depicted an exemplary graphical representation of the PLR response to a single bolus dose of hydromorphone. In FIG. 6, curve 610 corresponds to a baseline case, curves 620, 630, and 640, correspond to PLR observed sixty minutes, twenty minutes, and ten minutes post opioid intake. For the PLR depicted in FIG. 6 (upon intake of a bolus of hydromorphone), a strong negative correlation between constriction velocity and visual analog scale (VAS) was observed. The VAS is used to measure pain intensity based on a position along a continuous line between two endpoints (e.g., the left end point of the line corresponds to the case of "no pain", whereas the right end point of the line corresponds to "worst pain possible"). Note that the VAS may also be graded on a scale ranging from 1-10, wherein 1 correspond to the case of no-pain, and 10 corresponds to worst pain.

Figure 7:
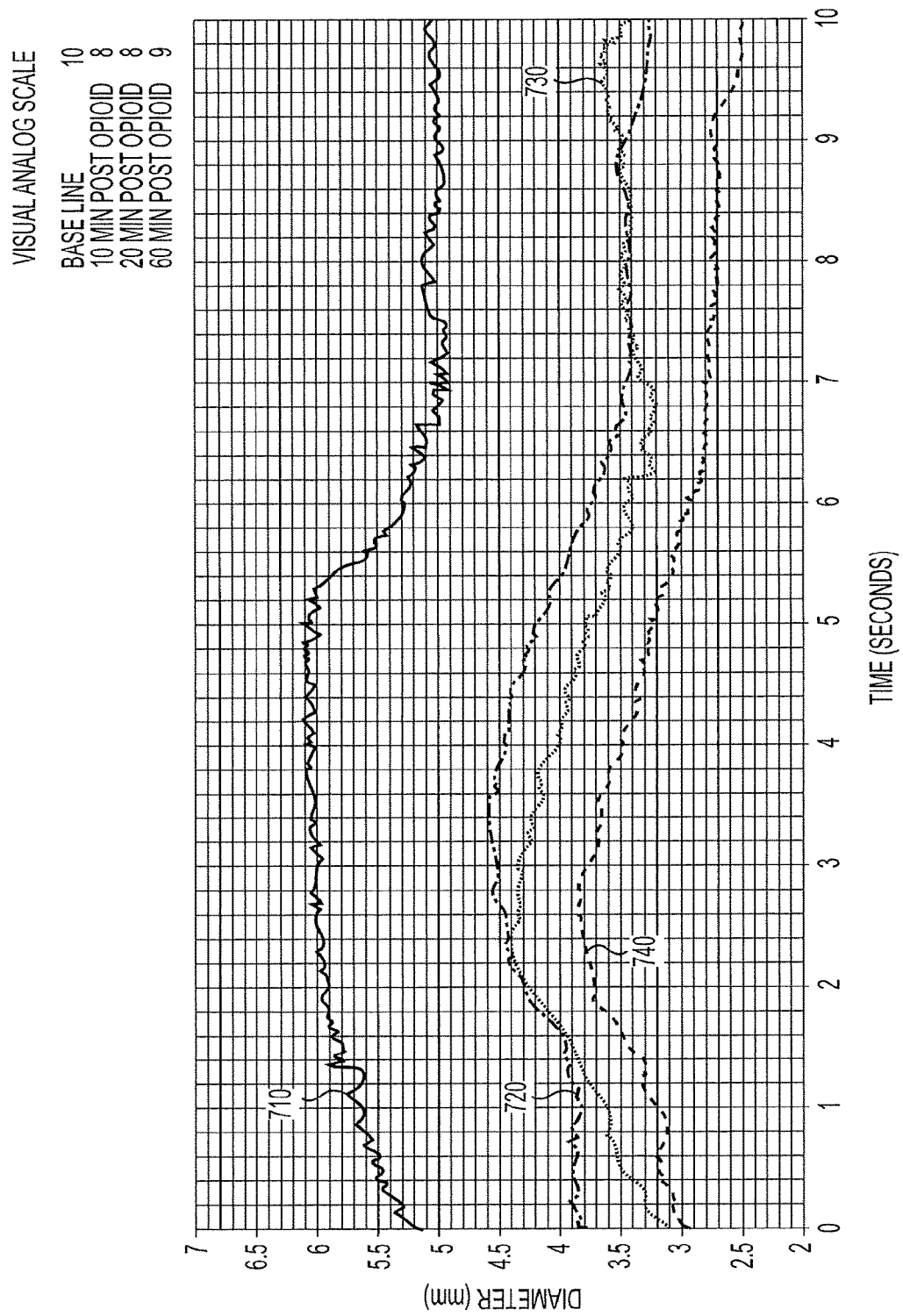
FIG. 7 depicts a graphical representation of the PRD response of the patient that has received the single bolus dose of hydromorphone.

FIG. 7 depicts a graphical representation of the PRD response to a 1 second of 5 Hz stimulus at 3 mA, which is performed on the patient that has received the single bolus dose of hydromorphone (of FIG. 6). In FIG. 7, curve 710 corresponds to a baseline case, curves 720, 730, and 740, correspond to pain profiles observed sixty minutes, twenty minutes, and ten minutes post opioid intake. Referring to FIG. 7, note that peak effect on amplitude and AUC occur at 10 minutes after injection, and reverse significantly at 60 minutes.

According to one embodiment, maximum constriction velocity (MCV) of the PLR correlates with pain intensity. For instance, MCV increases by 0.11 mm/s for every point increase in a 10-point visual analog scale. In the present embodiment, pain (nociception) is objectively measured via analysis of the PRD in response to neuro-specific stimuli, thereby allowing for the identification of types as well as intensity of pain. The present embodiment uses parameters of the PRD and PLR in the formulation of the acute and chronic pain indices. In the measurement of acute pain, parameters of the PRD including, but not limited to, the dilation amplitude (DA), MDV, the area under the curve (AUC) and the recovery time to baseline (RT) are used in the formulation of an acute pain index that 1. Measures pain or pain sensitivity. 2. Guides analgesic selection. 3. Guides dose response intervention. 4. Serves as a monitoring tool for repeated dosing. 5. Depending on the drug class being used can indicate tolerance. 6. Can detect pain, pain sensitivity or nociception in a conscious, sedated or unconscious patient. 7. Can assess the adequacy of a regional anesthetic block in conscious, sedated or unconscious patients.

By one embodiment, the MCV of the PLR can be used to quantify the subjective experience of pain. Accordingly, the MCV is incorporated into the pain -index so that elements of the subjective experience such as anxiety may be properly addressed (e.g., an anxiolytic vs. an opioid). The measurement of persistent, ongoing or chronic pain can be detected in a manner similar to that as described previously with respect to acute pain, but has unique impacts on the various parameters examined.

By one embodiment, large-fiber neuropathic pain is transmitted via Aβ nerve fiber type, which is stimulated at 2000 Hz. Neuropathic pain is detected and measured by examining the relationship of the parameters of the PRD to a 2000 Hz stimulus. Small fiber neuropathic pain is transmitted via C-fiber and Aδ fibers, and is often seen with metabolic disorders such as diabetes or chemotherapy induced neuropathic pain. The neuropathic pain index (NPI) integrates the intensity stimulus (mA) relative to the DV, DA, AUC and recovery time. Accordingly, neuropathic pain can be defined with respect to whether the pain is a small fiber based pain or a large fiber based pain. Moreover the NPI provisions for flexibility of monitoring an intervention.

Figure 8A:
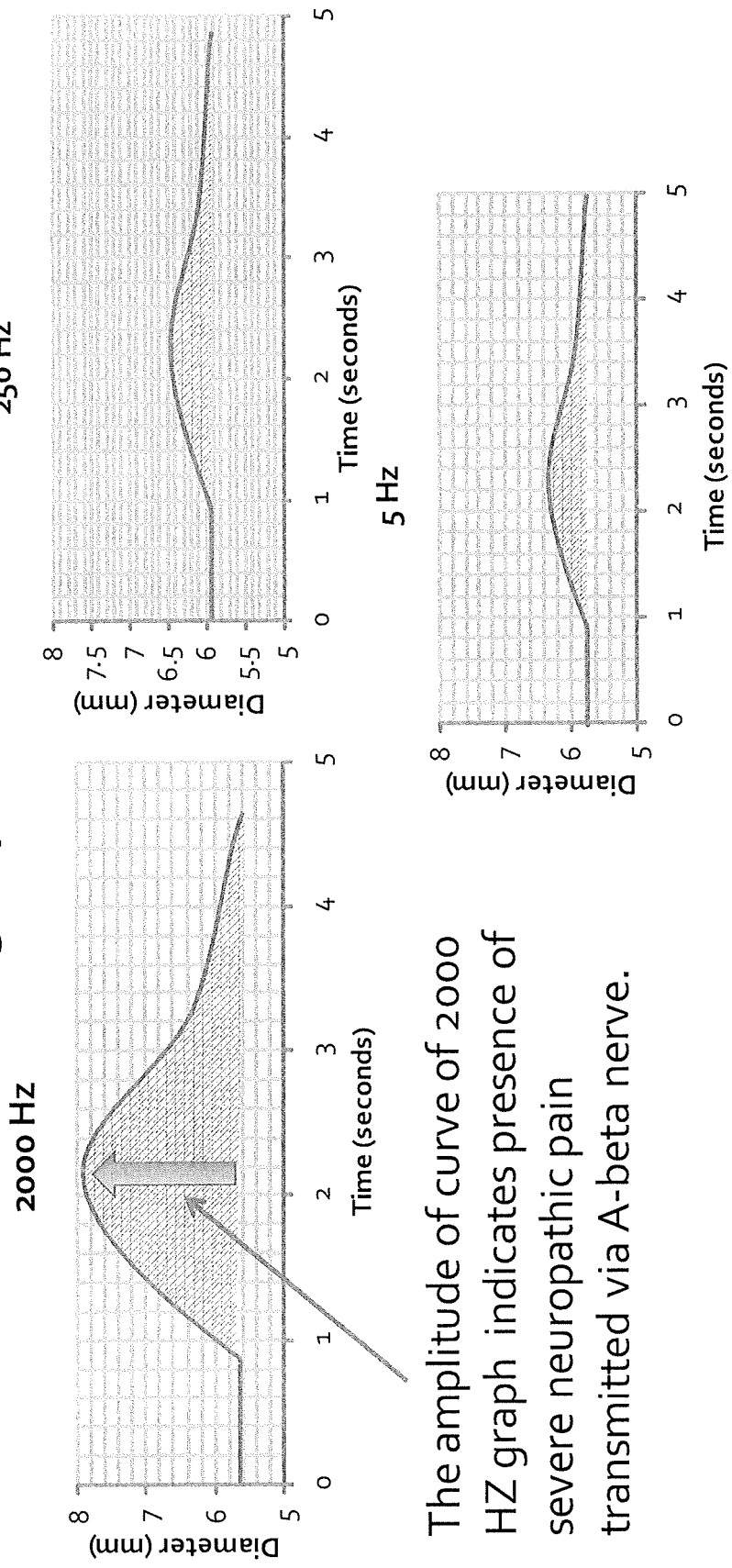
FIG. 8A illustrates an exemplary graph depicting the utilization of PRD in assessing sciatic nerve pain.
Figure 8B:
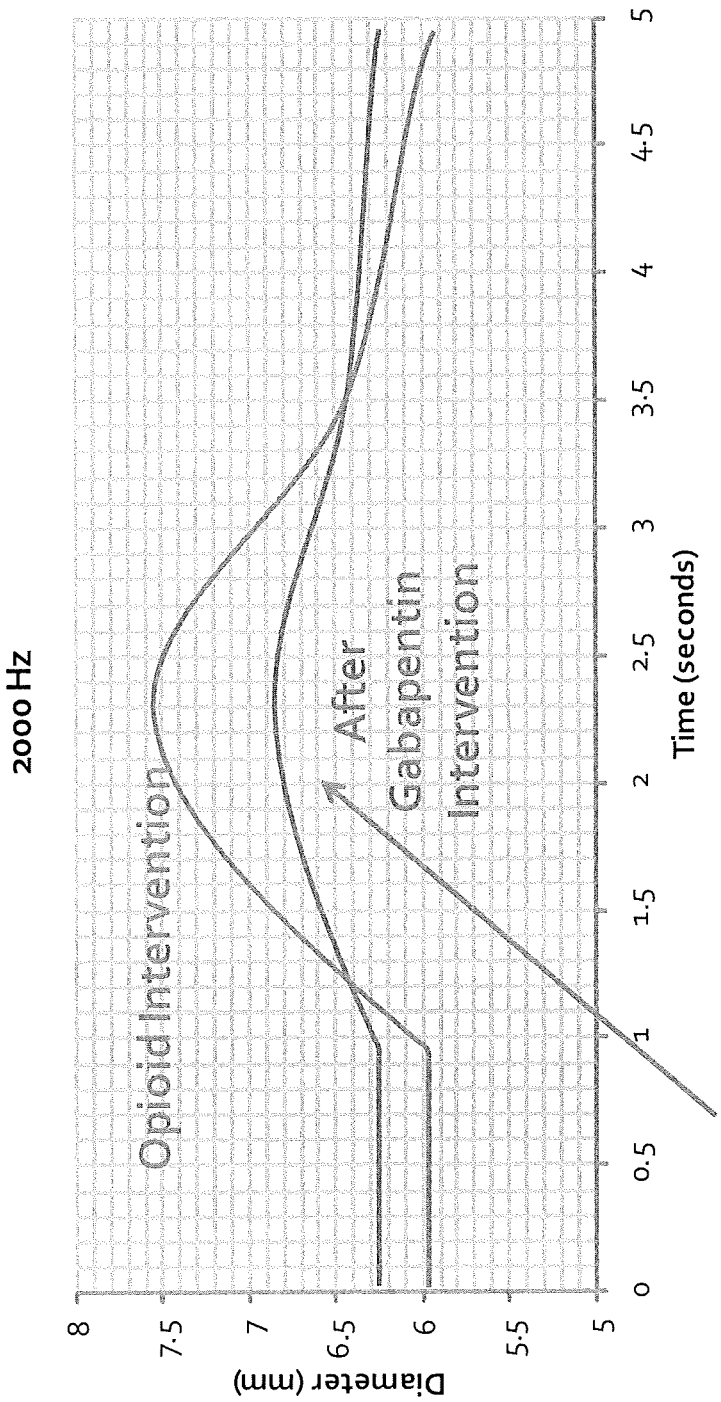
FIG. 8B illustrates according to an embodiment, a graph depicting a pharmacological assessment of the sciatic nerve pain.

FIG. 8A illustrates an exemplary graph depicting the utilization of PRD in assessing sciatic nerve pain. As shown in FIG. 8A, the amplitude of the curve corresponding to the 2000 Hz frequency substantially exceeds the amplitude of curves corresponding to the 250 Hz and 5 Hz frequencies, respectively. Accordingly, the largest pain sensitivity is produced along the Aβ nerve thereby indicating large fiber neuropathic pain. FIG. 8B illustrates according to an embodiment, a graph depicting a pharmacological assessment of the sciatic nerve pain. Referring to FIG. 8B, it can be observed that compression of the Aβ fiber is not amenable to opioid analgesia, whereas the drug Gabapentin diminishes the pain sensitivity. Note that the area under the curve corresponding the case of Gabapentin intervention is substantially smaller than the curve corresponding the case of opioid intervention.

As stated previously, embodiments of the present disclosure provide for a technique of creating a signature for each drug. One mechanism of achieving the signatures is by modeling the PLR to detect and identify impacts specific to the substances under consideration based on utilizing a Fourier transform analyses, and/or a dynamic-time-warping algorithm that include determining cross-correlation and root-mean-square deviation analysis with the curve shape features. By one embodiment, individual opioids are distinguishable from each other because of their non-mu mediated activity. For instance, mu-opioid receptor agonists/antagonists have a different profile from pure mu-opioid agonists with repeated dosing. Opioids with a neuro-excitatory 3-glucuronide metabolite (e.g., morphine and hydromorphone) have a diminished opioid profile when compared with pure mu-opioids without the metabolite. Moreover, patients with renal failure will manifest this sooner and in a more pronounced manner due to faster accumulation of the metabolite.

By one embodiment, other drugs, largely indicated for the management of neuropathic pain for which signatures are identified include, ketamine, gabapentin, pregabalin, selective serotonin reuptake inhibitors (SSRI), serotonin norepinephrine reuptake inhibitors SNRI, tricyclic antidepressants (TCA), monamine oxidase inhibitors (MAO), serotonin reuptake inhibiting anti-psychotics such as trazodone and 5HT2A and D2 receptor antagonist lurasidone and the like. According to one embodiment, cannabis and its constituent cannabinoids, such as tetrahydrocannabinol (THC) and cannabidiol (CBD) are fully characterized in terms of their impact on the shape of the PLR, and on their modulation of nociceptive and neuropathic pain as reflected by their impact on parameters of the PRD.

Figure 9:
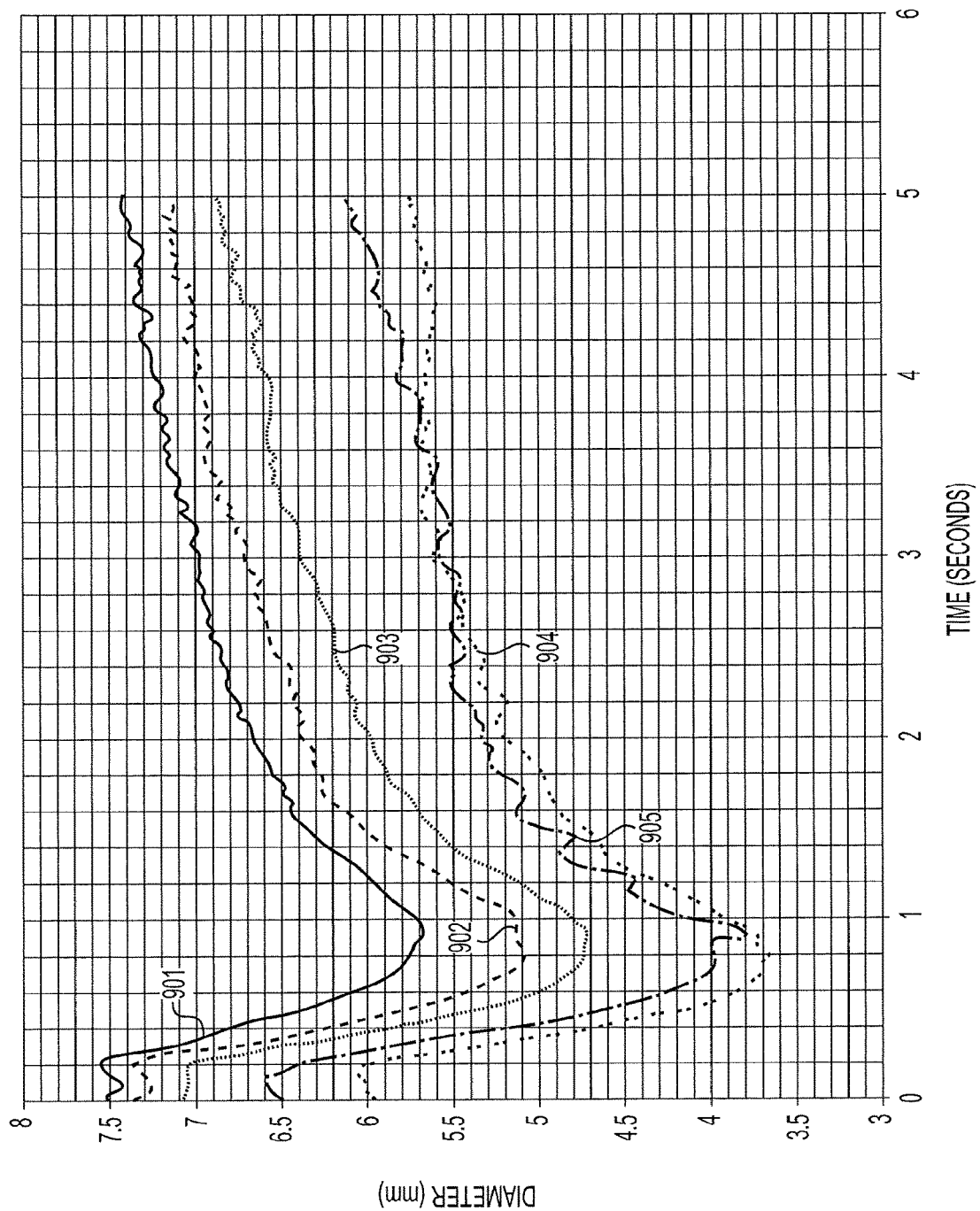
FIG. 9 depicts a graph illustrating an exemplary PLR after cannabis ingestion.
Figure 10:
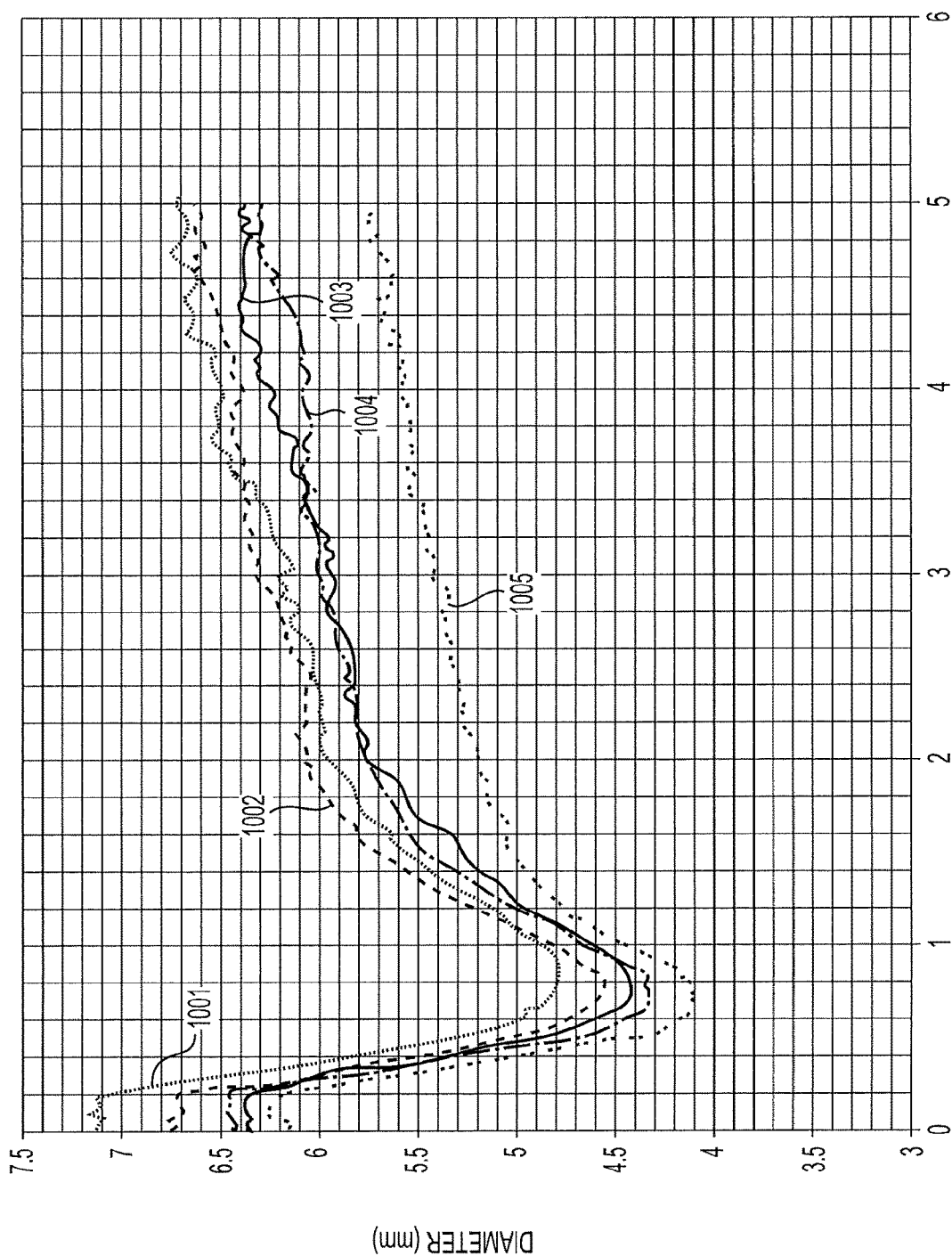
FIG. 10 depicts a graph illustrating an exemplary PLR after ingestion of half a dose of cannabis as that of FIG. 9.

FIG. 9 and FIG. 10 depict graphs illustrating recordings of the PLR in subjects that have ingested standardized quantities cannabis. FIG. 9 depicts PLR after cannabis ingestion, wherein curve 901 corresponds to a baseline case, curve 902 corresponds to the PLR after 30 minutes of cannabis ingestion, curve 903 corresponds to the PLR after 60 minutes of cannabis ingestion, curve 905 corresponds to the PLR after 120 minutes of cannabis ingestion, and curve 905 corresponds to the PLR after 180 minutes of cannabis ingestion. From FIG. 9, it is observed that there is a downward displacement of the PLR response with no significant changes in the PLR parameters other than resting pupil size. Moreover, a peak impact occurs at 180 minutes.

FIG. 10 depicts the PLR response after half of the cannabis dose ingestion as that of FIG. 9. It is observed that when the subject consumes half the dose of cannabis, the downward shift in the PLR is less than that produced when the subject ingests a whole dose. In FIG. 10, curve 1001 corresponds to PLR after 60 minutes of cannabis ingestion, curve 1002 corresponds to the PLR after 30 minutes of cannabis ingestion, curve 1003 corresponds to a baseline PLR, curve 1004 corresponds to the PLR after 120 minutes of cannabis ingestion, and curve 1005 corresponds to the PLR after 180 minutes of cannabis ingestion.

Modeling the shape of the PLR curves derives the pharmacodynamic signature for cannabis or any of its cannabinoid or terpenoid constituents. In this fashion, a cannabis detection tool and the ability to measure dose-ranging effects including psychotropic impairment when determining medical applications can be obtained. The use of cannabis and its constituents for the modulation of nociceptive and neuropathic pain is determined and monitored using a method similar to that described previously with respect to opioids except that both nociceptive and neuropathic pain can addressed.

Figure 11:
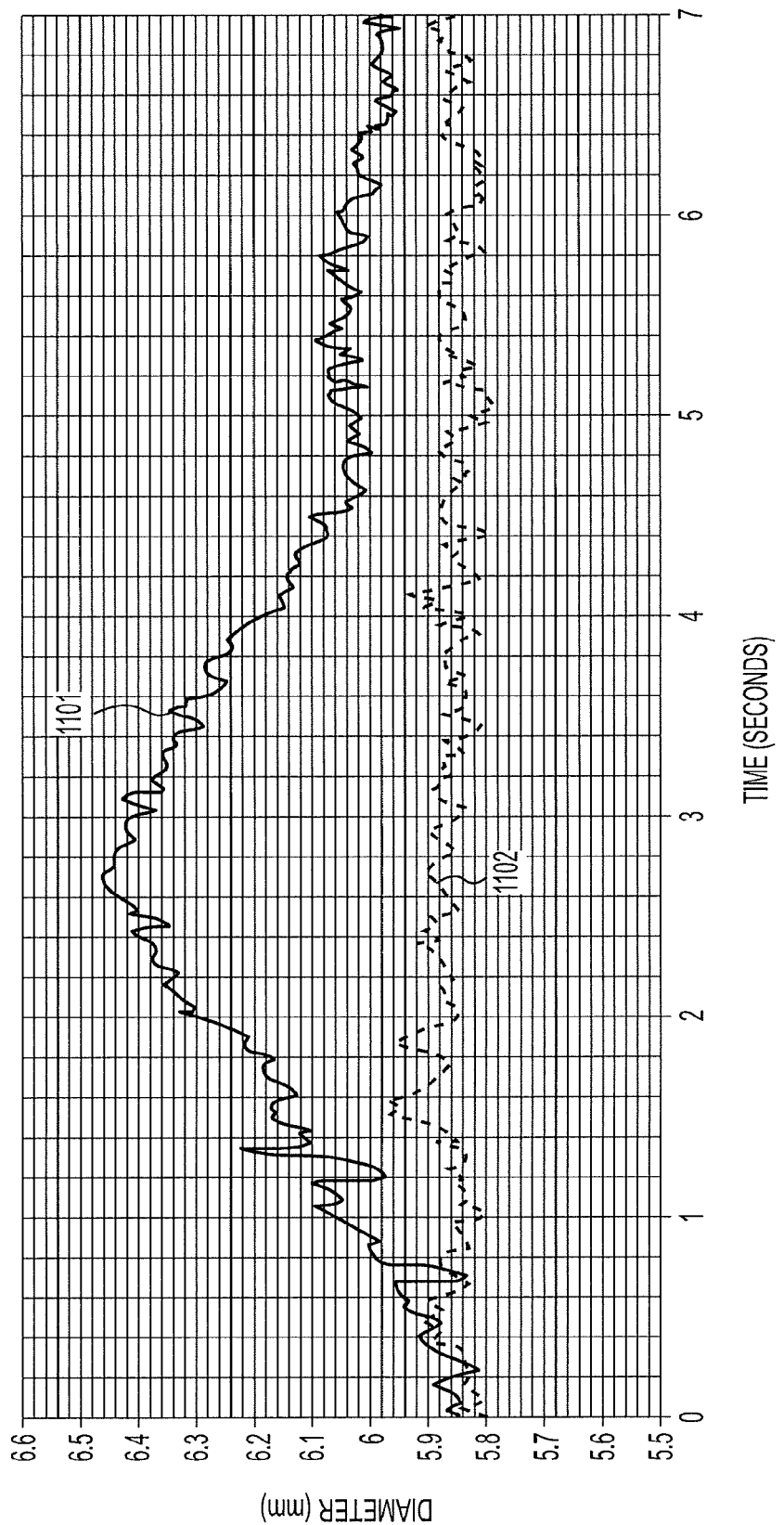
FIG. 11 depicts an exemplary pain profile PRD for cannabis.

Turning to FIG. 11 is depicted an exemplary graph illustrating a PRD for cannabis pain profile corresponding to a frequency of 250 Hz at 5 milli-amperes. Specifically, FIG. 11 depicts the ablation of pain sensitivity (obtained via area under the curve parameter of the PRD) mediated by the Aδ nerve at sixty minutes (curve 1102) after inhalation of vaporized cannabis. In FIG. 11, curve 1101 corresponds to a baseline curve. Note that after the time-duration of sixty minutes, a significant reduction in the area under curve is obtained.

Figure 12:
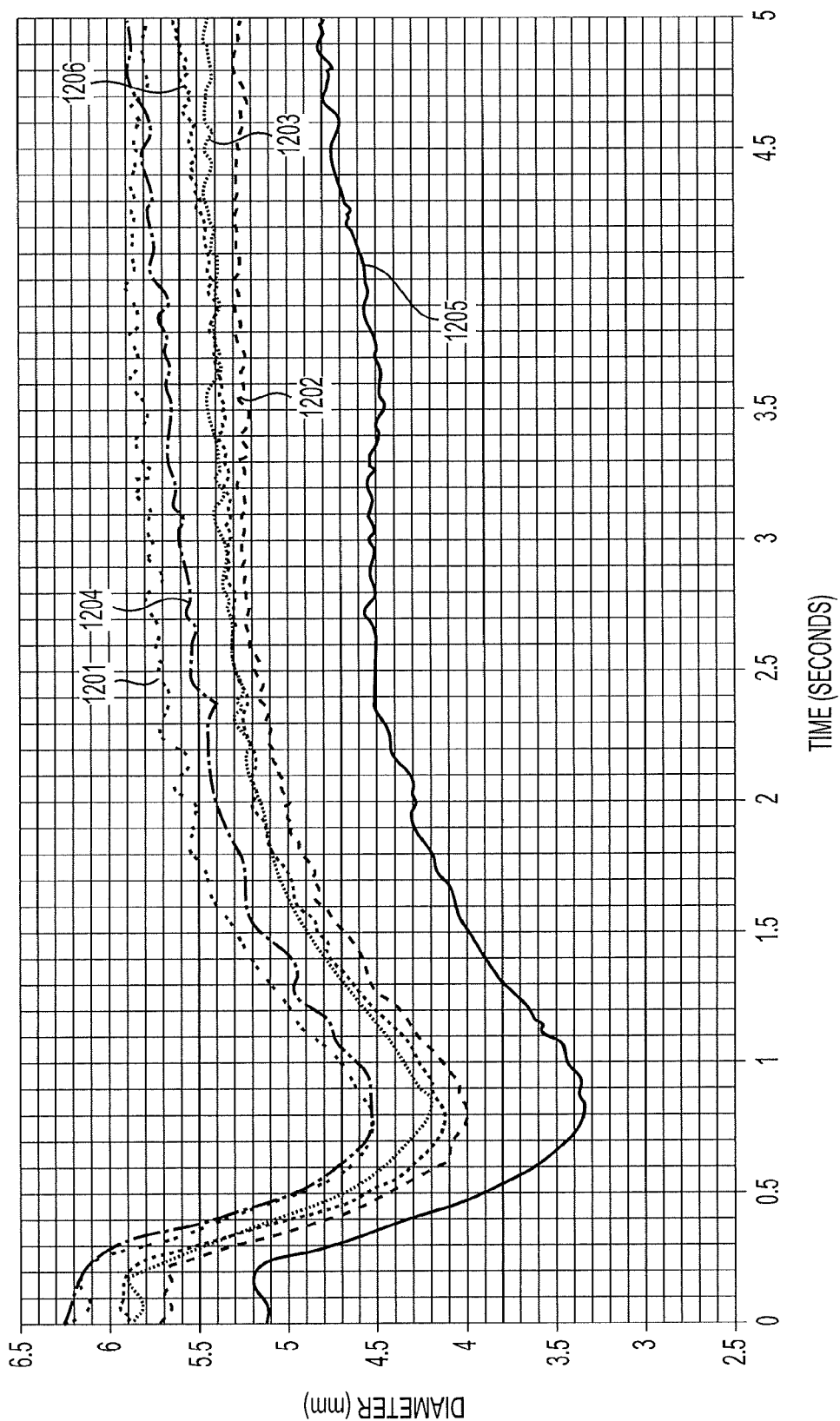
FIG. 12 depicts an exemplary cannabis pain profile illustrating tolerance.

Moreover, FIG. 12 depicts an exemplary graph demonstrating the acute effect of inhaled vaporized cannabis on an individual who is a chronic daily user of cannabis. It is observed that the tolerance profile reflected in the PLR response reflects an increase rather than decrease in pupil size as monitored over a three hour period. In FIG. 12, curve 1201 corresponds to a baseline case, curve 1202 corresponds to the PLR after 30 minutes of cannabis ingestion, curve 1203 corresponds to the PLR after 60 minutes of cannabis ingestion, curve 1205 corresponds to the PLR after 120 minutes of cannabis ingestion, and curve 1205 corresponds to the PLR after 180 minutes of cannabis ingestion.

By one embodiment of the present disclosure is provided a method of detecting diabetic neuropathy. Diabetic neuropathy is detected when there is a significant reduction in the pupil to iris ratio and/or a significant increase in the latency of the PLR, which is indicative of a dysautonomia. In addition to the detection of dysautonomia, the method by one embodiment, also objectively characterizes diabetic neuropathy. Specifically, using parameters of the PLR, indicia of dysautonomia are detected and identified. Patients with a disease duration of 10 years or greater, often manifest this symptomatology including increased latency of response and decreased CV. A dysautonomia index that includes the ratio of the product of the CV and latency over the resting pupil size serves as an indicator of the severity of the dysfunction. As the impairment progresses, neuropathic pain develops and can be evaluated using the 2000 Hz PRD. The method is similar to that of the evaluation of neuropathic pain described previously, with the probe application being on the affected extremity. Longitudinal evaluation and monitoring of pain and of an intervention such as duloxetine, milnacipran, and pregabalin is performed using the same method as for opioids but producing a PRD for all 3 fiber types that are affected.

By one embodiment, the above described techniques of determining opioid conditions, cannabis conditions and the like can be applied to detect depression as well as detection of pain sensitivity in depressive disorders and monitoring of anti-depressive drugs, including but not limited to TCAs, SSRI, SNRI, MAO inhibitors, NMDA antagonists, antipsychotics and cannabinoids.

By one embodiment, an important advantage incurred in using electrical stimulation to assess pain, and target specific sensory nerve fibers rather than traditional injury-producing stimulation techniques such as thermal, chemical, and mechanical stimuli, is that the electrical stimulation bypasses the peripheral nociceptors and stimulates the targeted nerve fiber directly. As a result, receptor-dependent processes such as accommodation (i.e., intensification of stimulus needed to elicit the same response) and habituation (i.e., reduced or inhibited responsiveness during repeated stimulation) do not occur. Thus, use of electrical stimulation not only allows the characterization of the nociceptive pathways carried by the individual sensory nerve types, it also provisions for repeated testing of nerve specific fibers without inducing injury.

Additionally, by one embodiment of the present disclosure, the neuro-stimulation is performed by utilizing electrical stimulation that is at a level below what is generally considered or perceived as painful or noxious to the patients, in order to determine their respective SDTs. Such "sub-noxious" neuro-specific stimulation is applied by generating electrical stimulation with an intensity that is large enough to achieve the targeted nerve fibers threshold action potential, but small enough that the patient does not consciously perceive a feeling of pain in response to that electrical stimulation. Accordingly, sub-noxious electrical stimulation applied at neuro-specific frequencies (e.g., 5 Hz and 250 Hz) can thereby be used to achieve threshold action potentials for Aδ and C fibers, separately, without the patient actually perceiving pain.

An aspect of the present disclosure utilizes a novel combination of neuro-specific electrical stimulation and PRD monitoring, wherein the neuro-specific electrical stimulation is directly correlated to the monitored pupil reactivity in real time to provide an objective measurement of pain sensitivity and analgesia. Accordingly, such measurements are utilized to provide an objective quantification of pain sensitivity (e.g., a pain score, an SDT value, or the like), to provide an objective measurement of the effect of currently used analgesics, and other pain interventions, to provide an objective measurement of the efficacy and dose-response relationships of newly developed and/or investigational drugs, and other interventions targeted for the management of pain, to identify the onset of tolerance and/or analgesic-induced toxicity, and to provide an objective characterization of pain (e.g., nociceptive pain, neuropathic pain, hyperalgesia, allodynia, etc.).

Figure 13A:
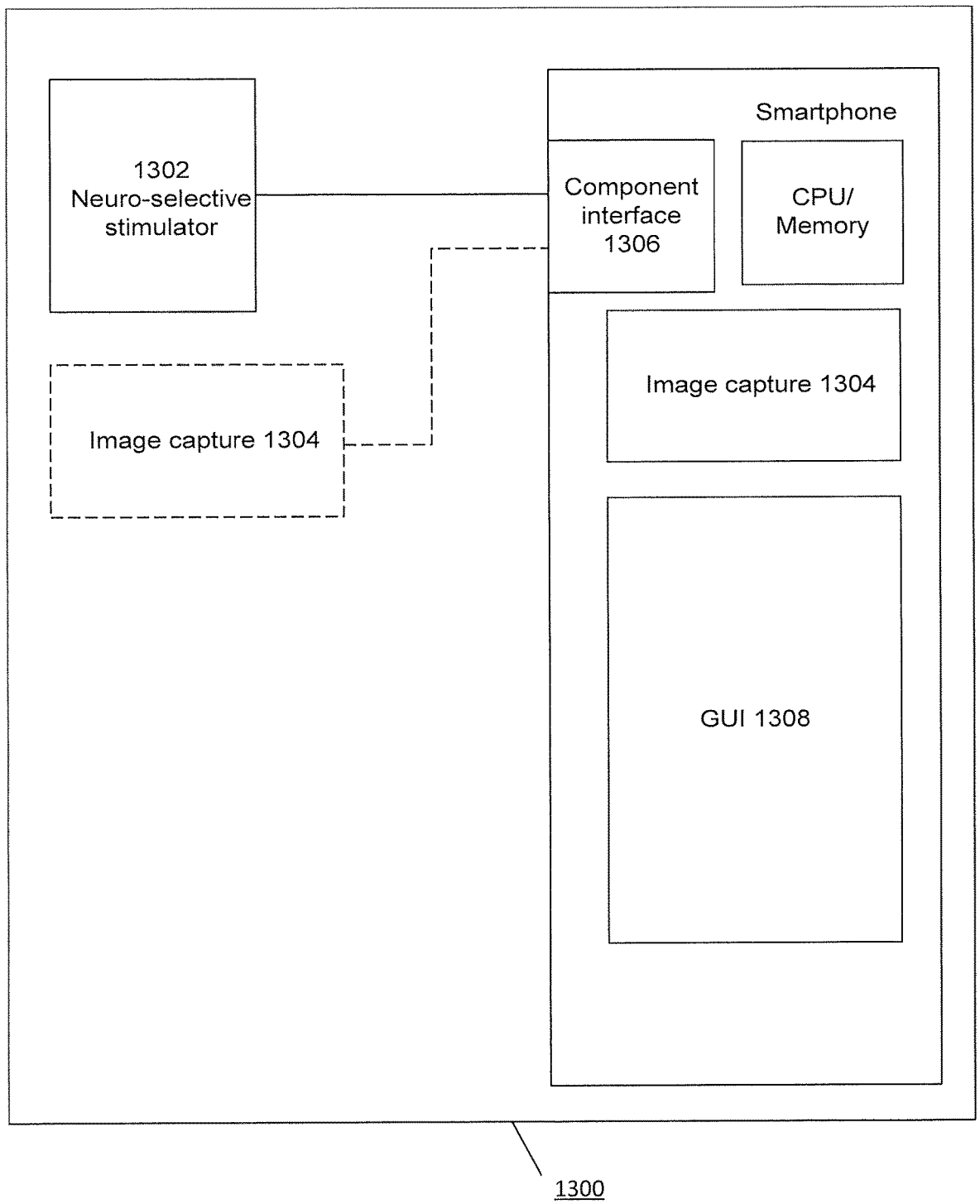
FIG. 13A illustrates an exemplary pupil-algometer according to one embodiment.

By one embodiment, as described next, the above described functionalities can be provided by a single device, referred to as a "pupil-algometer". FIG. 13A illustrates an example of a pupil-algometer 1300 according to an embodiment of the present disclosure. The pupil-algometer 1300 includes a neuro-selective stimulator 1302, a pupilometer measuring PRD and/or PLR 1304, a component interface 1306, and a graphical user interface 1308 (the phone's screen).

It must be appreciated that the elements 1302 and 1304 as shown in FIG. 13A, may be integral, or add on hardware components to a smartphone. Components 1306 and 1308 are all integral to the smartphone platform. The neuro-selective stimulator 1302 is configured to apply neuro-specific stimulation to specific nerve fibers (e.g., Aβ, Aδ, and C-fibers) using specific voltages and currents applied at neuro-specific frequencies (i.e., 2000, 250, and 5 Hz). The PRD 1304 is configured to monitor PRD based on neuro-physiological responses to the neuro-specific electrical stimulation generated by the neuro-selective stimulator 1302 and/or to other forms of stimulation (e.g. surgical pain, point tenderness of fibromyalgia etc.)

The component interface 1306 is configured to control both the neuro-selective stimulator 1302 and the PRD monitor 1304, to integrate the functionality of those two components 1302 and 1304, and to store the data (either on the phone or in a cloud based data collection platform) obtained with those two components 1302 and 1304. The graphical user interface (smartphone) 1308 is configured to receive and transmit data that is input by a user to control the neuro-selective stimulator 1302 and the PRD monitor 1304 and to analyze and display the data that is measured, sampled, and stored with the three components 1302, 1304, and 1306.

Figure 13B:
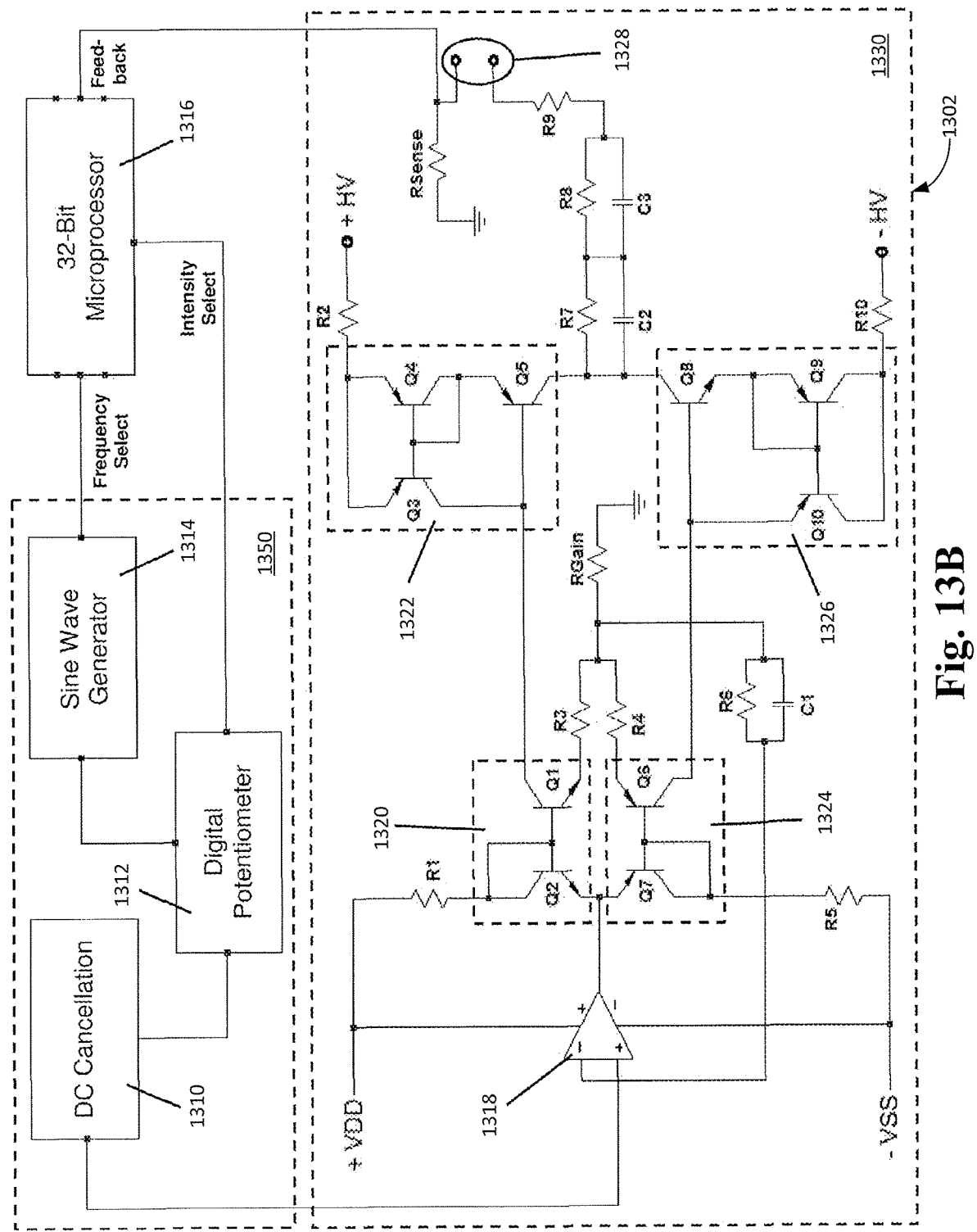
FIG. 13B illustrates an exemplary neuro-selective stimulator.

FIG. 13B illustrates according to an embodiment, the neuro-selective stimulator 1302. The neuro-selective stimulator 1302 includes a low-voltage circuit 1350 and a high-voltage circuit 1330. The low-voltage circuit 1350 and the high-voltage circuit 1330 are both connected to a microprocessor 1316 (e.g. included in a smartphone as shown in FIG. 13A) via the component interface 1306. The low-voltage circuit 1350 includes a sine wave generator circuit 1314, a digital potentiometer circuit 1312, and a DC cancellation circuit 1310. The high-voltage circuit 1330 includes a precision non-inverting operational amplifier (op-amp) 1318, a first current mirror 1320, a second current mirror 1324, a first high voltage current source 1322, a second high voltage current source 1326, and electrode inputs/outputs 1328. The low-voltage circuit 1350 generates a pure AC sine wave signal that is converted to a current based signal by the high-voltage circuit 1330.

The sine wave generator circuit 1314 and the microprocessor 1316 are both connected to the digital potentiometer circuit 1312. The sine wave generator circuit 1314 sends the sine wave it generates to the digital potentiometer circuit 1312. The microprocessor 1316 sends commands (e.g. "Intensity Select") to the digital potentiometer circuit 1312 that correspond to different signal amplitudes, which are used by a voltage divider at the digital potentiometer circuit 1312 to apply different signal amplitudes to the sine waves generated by the sine wave generator circuit 1314. Those signal amplitudes are precisely controlled by the microprocessor 1316 so they can be used by the high-voltage circuit 1330 to generate currents with different intensities (e.g., 0.5, 0.85, and 2.3 mA) that correspond to the stimulus required to activate different nerve fibers (e.g., C, Aδ, and Aβ fibers). The maximum intensity generated by the high-voltage circuit 1330 is set such that only sub-noxious stimulus is applied to a patient (i.e., an intensity large enough to achieve the targeted nerve fiber's threshold action potential but small enough that the patient does not consciously perceive a feeling of pain).

The digital potentiometer circuit 1312 is connected to the DC cancellation circuit 1310 and sends the signals generated with the input from the microprocessor 1316 and the sine wave generator circuit 1310 to the DC cancellation circuit 1310. The DC cancellation circuit 1310 removes the DC components from those signals, thereby producing a pure AC signal with the desired frequency and amplitude. The resulting voltage-based signal is then sent to the high-voltage circuit 1330 for conversion into a current-based signal.

The DC cancellation circuit 1310 of the low-voltage circuit 1350 is connected to the non-inverting input of the non-inverting op-amp 1318 of the high-voltage circuit 1330. A precision gain resistor $R_{Gain}$ is connected to the inverting input of the non-inverting op-amp 1318 through a resistor-capacitor combination $R_6/C_1$. The DC cancellation circuit 1310 sends the voltage-based sine wave signal generated with the input from the digital potentiometer circuit 1312 to the non-inverting op-amp 1318 while the gain resistor $R_{Gain}$ is used to control the gain of the high-voltage circuit 1330. The non-inverting op-amp 1318 preferably has input bias currents of less than a few pico-amperes (pA), and the gain resistor $R_{Gain}$ preferably has a resistance of approximately 10 ohms.

The non-inverting op-amp 1318 is connected to the first transistors $Q_2$ and $Q_7$ of the first and second current mirrors 1320 and 1324, respectively. The second transistors $Q_1$ and $Q_6$ of the first and second current mirrors 1320 and 1324 are connected to the gain resistor $R_{Gain}$ and the non-inverting input of the non-inverting op-amp 1318 through resistors $R_1$ and $R_5$, respectively. The first and second transistors $Q_2$ and $Q_1$ of the first current mirror 1320 are NPN transistors, and the first and second transistors $Q_7$ and $Q_6$ of the second current mirror 1324 are PNP transistors.

The second transistors $Q_1$ and $Q_6$ of the first and second current mirrors 1320 and 1324 are connected to the first transistors $Q_3$ and $Q_{10}$ of the first and second high voltage current sources 1322 and 1326, respectively, and outputs of the first and second current mirrors 1320 and 1324 are sent to the first and second high voltage current sources 1322 and 1326, respectively. High voltage sources +HV (e.g., +400 V) and −V (e.g., −400 V) are connected to the second transistors $Q_4$ and $Q_9$ of the first and second high voltage current sources 1322 and 1326 through resistors $R_2$ and $R_{10}$, respectively. The third transistors $Q_5$ and $Q_8$ of the first and second high voltage current sources 1322 and 1326 are connected to the electrode inputs/outputs 1328 through a resistor $R_9$ and a pair of resistor-capacitor combinations $R_7/C_2$ and $R_8/C_3$ in series. The first, second, and third transistors $Q_3$, $Q_4$, and $Q_5$ of the first high voltage current source 1322 are PNP transistors, and the first, second, and third transistors $Q_{10}$, $Q_9$, and $Q_8$ of the second high voltage current source 1326 are NPN transistors. Together, the components of the high-voltage circuit 1330 operate as a voltage-to-current converter capable of generating current stimuli with intensities of 10 mA and greater.

The electrode inputs/outputs 1328 of the high-voltage circuit 1330 are connected to a current measuring resistor and to the microprocessor (smartphone) 1316. The outputs of the first and second current mirrors 1320 and 1324 are combined and sent to the electrode inputs/outputs 1328 via the pair of resistor-capacitor combinations $R_7/C_2$ and $R_8/C_3$ to provide further DC cancellation and to compensation for changes in a patient's skin impedance. Further, the resulting current that is applied to a patient is measured through the measuring resistor $R_{Sense}$ and sent back to the microprocessor 1316 for fine adjustment (e.g. "Feedback"). For example, the microprocessor 1316 may automatically reduce the intensity of the current if it is measured to be higher than the current that is required to target the desired nerve fiber and/or higher than the threshold current for producing sub-noxious stimulation. In such a fashion, the low-voltage circuit 1350 provides for the precise control of the frequency and amplitude of the desired signal, and the high-voltage circuit 1330 provides for precise voltage-to-current conversion.

The electrode inputs/outputs 1328 are connected to electrodes through corresponding electrode cables. The electrodes provide a consistent, distortion free interface between the neuro-selective stimulator and a patient's skin. The electrodes are preferably gold plated and paired together using a flexible spreader to standardize the distance between them or exist as a probe to facilitate dental applications and testing of cutaneous regions of allodynia. The electrodes are also preferably cupped to accommodate electrode gel for maintaining a consistent output current density for reliable, repeatable results. Electrodes fashioned at the end of a handheld probe are used in instances where such things including but not limited to dental pain, neuropathic (e.g., allodynia) or nociceptive (e.g., wound pain or sensitivity) skin pain, headache evaluation (vascular vs. tension) and objective measure of pressure point tenderness of fibromyalgia. The electrode cables are lightweight lead wires that are terminated with spring loaded molded portions configured to resiliently hold the electrodes. The electrodes and electrode cables may be reusable or disposable and designed for single-use only. The algometer is configured to operate using commercially available electrodes and electrode cables, which helps reduce the manufacturing and operational costs of the algometer 1300.

Moreover, the smartphone may include a lumen meter to provide a measure of the ambient light that can then be used to normalize any data that is compared to normative data, and an ability to adjust the intensity of the flash. The intensity may be, for example, between 200 and 600 Lux.

Figure 14:
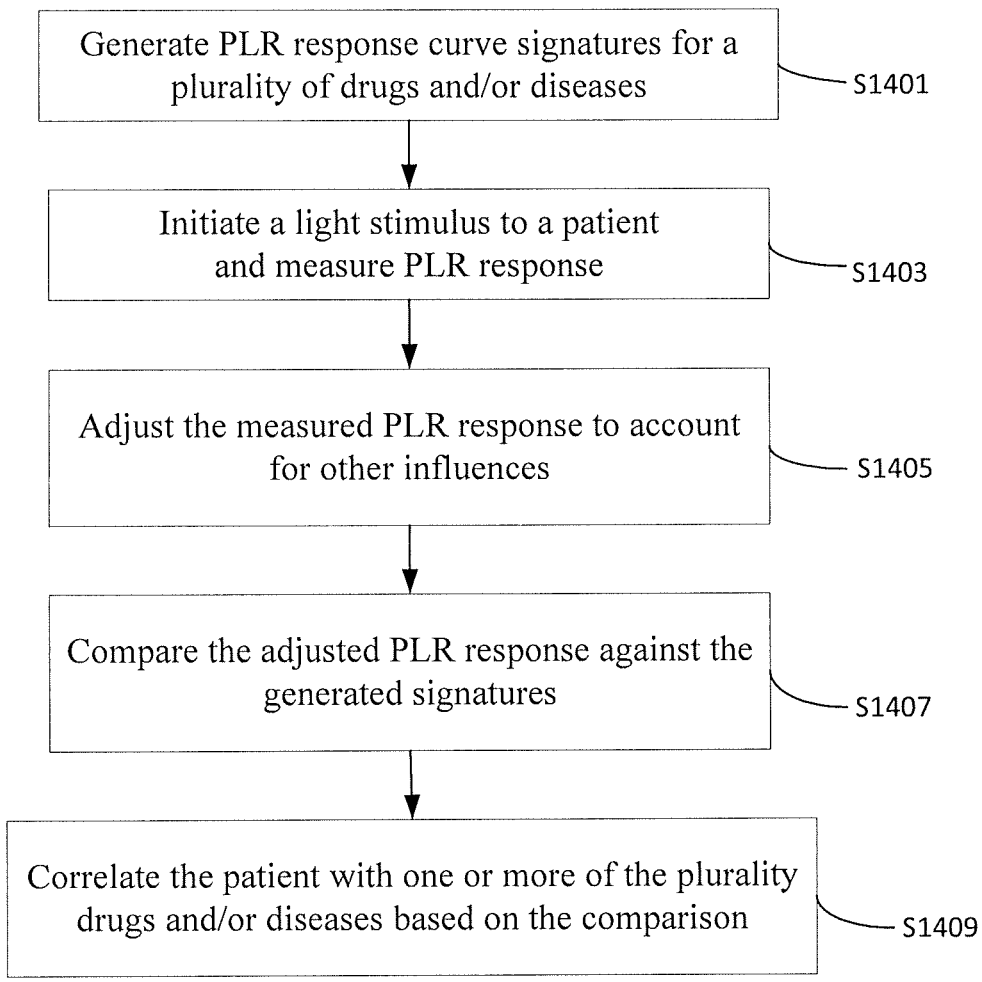
FIG. 14 depicts an exemplary flowchart illustrating a process for detecting patient disease or patient drug use based on a PLR response of the patient.

Turning now to FIG. 14 is depicted an exemplary flowchart illustrating a process for detecting patient disease or patient drug use based on a PLR response of the patient. The process commences in step S1401, wherein PLR response curve signatures for a plurality of drugs and/or diseases are generated.

In step S1403, a light stimulus is initiated to the patient and the PLR response is measured. Further, the process moves to step S1405, wherein the measured PLR response is adjusted to account for other influences. For instance, as stated previously, the MCV of the PLR Is used to quantify the subjective experience of pain and the parameter MCV can be incorporated in the pain index so that elements of the subjective experience such as anxiety may be appropriately addressed.

The process moves to step S1407, wherein the adjusted PLR response is compared against the generated signatures. Further, in step S1409, the patient is correlated with one or more of the plurality of drugs and/or diseases based on the comparison.

Figure 15:
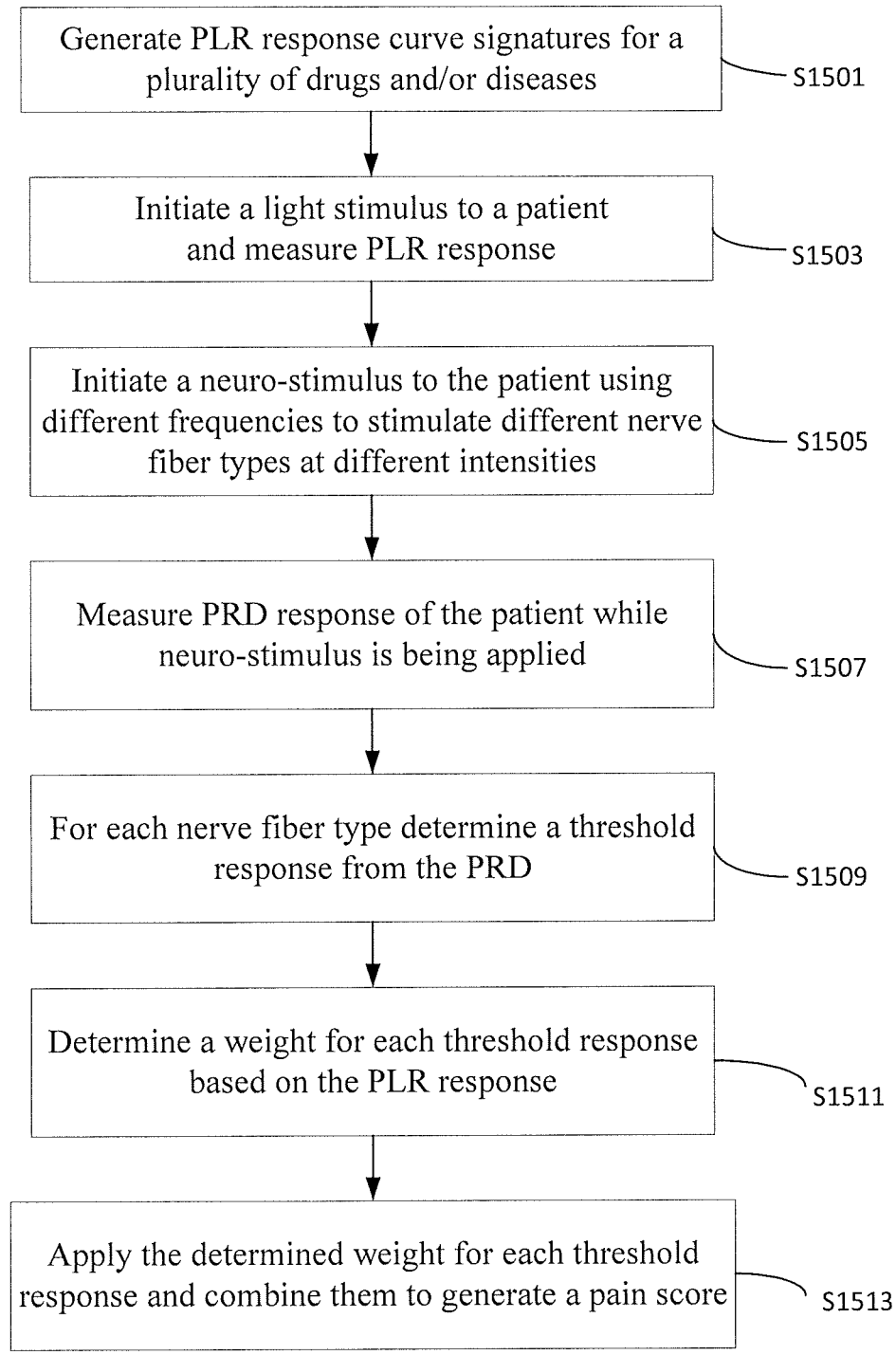
FIG. 15 depicts an exemplary flowchart depicting the steps performed to generate a pain score.

FIG. 15 depicts an exemplary flowchart illustrating the steps performed in determining a pain score. In step S1501, PLR response curve signatures for a plurality of drugs and/or diseases are generated. In step S1503, a light stimulus is initiated to a patient and the PLR response is measured.

Further, in step S1505, a neuro-stimulus is initiated to the patient using different frequencies to stimulate different nerve fiber types at different intensities.

In step S1507, while the neuro-stimulus is being applied over the different frequencies and over different intensities, the PRD response of the patient is measured.

The process in step S1509, determines, for each nerve fiber type, a threshold response from the PRD. Further, the process moves to step S1511, wherein a weight for each threshold response is determined based on the PLR response. The process in step S1513 generates a pain score by combining the determined weight for each threshold response. For instance, by one embodiment, a pain score e.g. pain sensitivity index (PSI) can be derived from the area under the curve of the PRD divided by the sensory detection threshold (SDT) (mA) and noting that a PSI at 2000 Hz which is greater than or equal to a PSI at 250 Hz or a PSI at 5 Hz, would indicate neuropathic pain, whereas the reverse would indicate nociceptive pain. Upon generating the pain score in step S1513, the process as depicted in FIG. 15 terminates.

It must be appreciated that the techniques of the above described embodiments can be applied in a variety of other applications. For instance, the above embodiments may be applied in dental scenario. The dental pulp includes only C-fibers and Aδ fibers. Pulp vitality is therefore achieved by applying the stimulating electrodes directly to a tooth and determining if the correct tooth is being addressed and if a root canal is indicated. Pulp vitality is questionable if a 5 Hz PRD is produced. Dental sensitivity to cold is often confirmed by the production of a 250 Hz PRD. The modeling of the PRD curves weighs the impact of the threshold response, which also provisions for the comparison among individuals.

By one embodiment, the PRD can be used to objectively measure the impact on pain sensitivity of a non-pharmacologic intervention (e.g., acupuncture, chiropractic, cognitive behavioral therapy etc.). In the assessment of non-pharmacological interventions, the impact of interventions including but not limited to physical therapy, acupuncture, cognitive behavioral therapy, chiropractic etc. may be assessed by performing pre and post neuro-stimulation query in order to quantify their anti-nociceptive effect. The PRD threshold responses among the 3 frequencies can be modeled to determine the relative contribution of the fiber types to generate a characterization of the pain type sensitivity and quantify the anti-nociceptive impact produced by the interventions.

By one embodiment, the techniques of the present disclosure provision for an opioid toxicity management tool. The weighted parameters of the PLR and PRD as well as respiratory rate and heart rate can be incorporated into an algorithm (such as time-warping algorithms, Fourier analyses and the like) to determine the presence of opioid toxicity (overdose) and guide titration of opioid reversal (e.g., naloxone, naltrexone etc.) to avoid precipitant withdrawal. In a similar manner, opioid sparing effects of adjuvants (e.g., cannabinoids, NSAIDs, alpha-2 agonists, gabapentinoids, SSRIs, etc.) can be objectively quantified by integrating weighted features of the PLR and 5 Hz PRD. Moreover, by one embodiment, CYP2D6 phenotyping can be performed by using codeine as a probe drug and obtaining the PLR response at timed intervals to detect the production/presence of morphine. The magnitude of the response provides an indication as to whether an individual has a slow, rapid, or ultra-rapid metabolic rate.

Moreover, an aspect of the present disclosure also provides for the feature of profiling diseases. Specifically, disease profiles can be established by modeling the PLR in order to detect disease-specific impact on the PLR. Examples include the dysautonomia occurring in postural orthostatic tachycardia syndrome and diabetes where both a dysautonomia and neuropathy can be identified. Disorders include but are not limited to diabetes, POTS, voiding disorders, autism spectrum disorder, fibromyalgia and concussion. Furthermore, the techniques described herein can be applied to canines. Specifically canines have a pupillary reflex that is the same as that observed in humans. PLR and clinical PRDs can thus be obtained for canines and assessed in a manner similar to that as for humans.

Moreover, the methodologies presented herein with respect to the PLR and PRD may be applied to a vast variety of patients. Specifically, the method can be used in preterm infants 30 weeks post conceptual age through senescence, in verbal and non-verbal individuals, and in conscious, anesthetized and unconscious individuals. Furthermore, ass stated previously, the pupil algometer can be integrated with a smartphone. The smartphone-based pupilometer may use infrared to determine focal length between the camera and the subject and a lumen meter to determine ambient light. Such variables can be accounted by the algorithms (time-warping etc.) to obviate the need for an eye cup and allow for monitoring to occur from a couple of feet away.

Each of the functions of the described embodiments may be implemented by one or more processing circuits. A processing circuit includes a programmed processor (for example, processor 1603 in FIG. 16), as a processor includes circuitry. A processing circuit also includes devices such as an application-specific integrated circuit (ASIC) and circuit components arranged to perform the recited functions.

Figure 16:
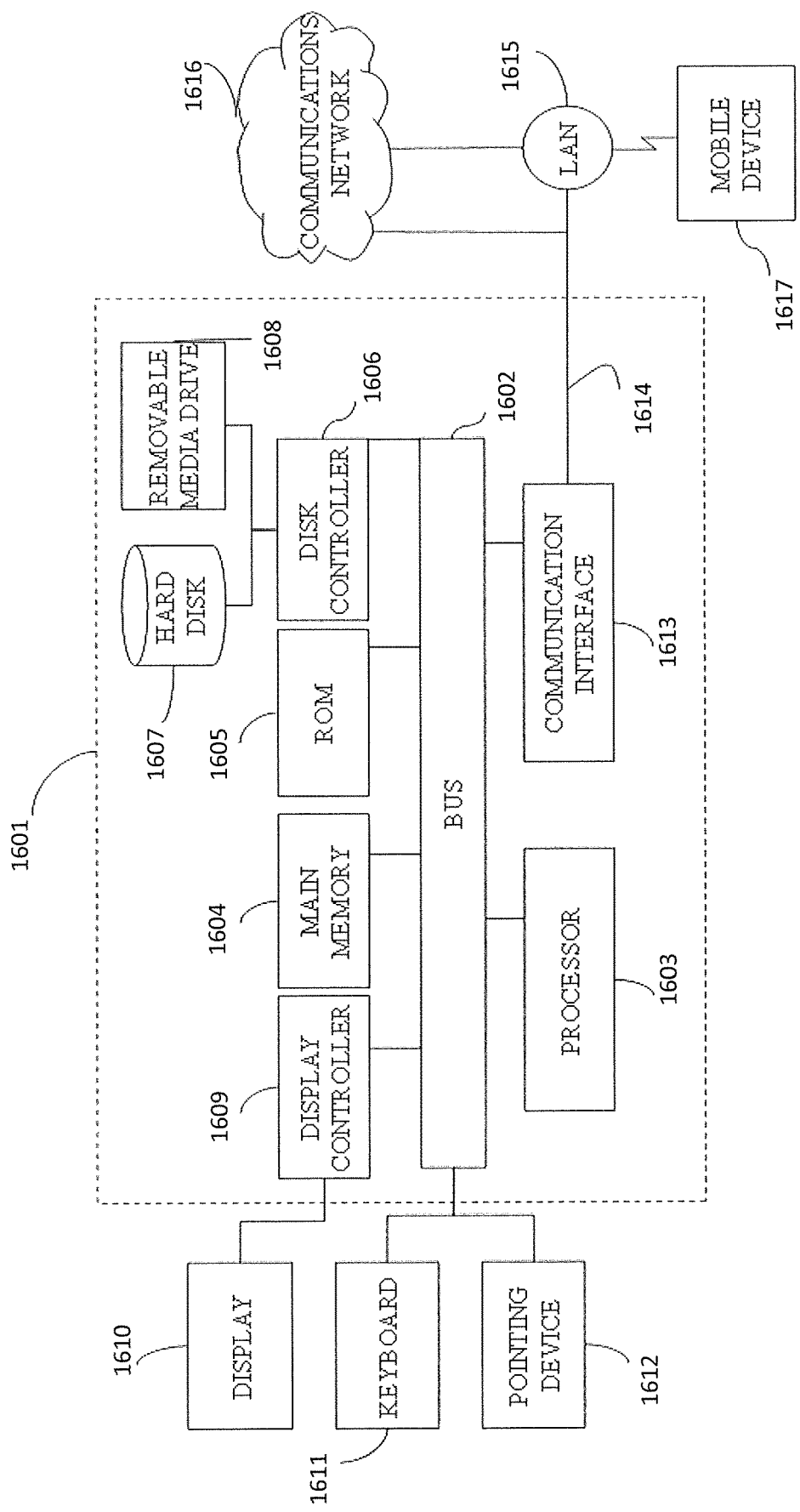
FIG. 16 illustrates a block diagram of a computing device according to one embodiment.

The various features discussed above may be implemented by a computer system (or programmable logic). FIG. 16 illustrates such a computer system 1601. In one embodiment, the computer system 1601 is a particular, special-purpose machine when the processor 1603 is programmed to perform monitoring, authentication and evaluation processes.

The computer system 1601 includes a disk controller 1606 coupled to the bus 1602 to control one or more storage devices for storing information and instructions, such as a magnetic hard disk 1607, and a removable media drive 1608 (e.g., floppy disk drive, read-only compact disc drive, read/write compact disc drive, compact disc jukebox, tape drive, and removable magneto-optical drive). The storage devices may be added to the computer system 1601 using an appropriate device interface (e.g., small computer system interface (SCSI), integrated device electronics (IDE), enhanced-IDE (E-IDE), direct memory access (DMA), or ultra-DMA).

The computer system 1601 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1601 may also include a display controller 1609 coupled to the bus 1602 to control a display 1610, for displaying information to a computer user. The computer system includes input devices, such as a keyboard 1611 and a pointing device 1612, for interacting with a computer user and providing information to the processor 1603. The pointing device 1612, for example, may be a mouse, a trackball, a finger for a touch screen sensor, or a pointing stick for communicating direction information and command selections to the processor 1603 and for controlling cursor movement on the display 1610.

The processor 1603 executes one or more sequences of one or more instructions contained in a memory, such as the main memory 1604. Such instructions may be read into the main memory 1604 from another computer readable medium, such as a hard disk 1607 or a removable media drive 1608. One or more processors in a multi-processing arrangement may also be employed to execute the sequences of instructions contained in main memory 1604. In alternative embodiments, hard-wired circuitry may be used in place of or in combination with software instructions. Thus, embodiments are not limited to any specific combination of hardware circuitry and software.

As stated above, the computer system 1601 includes at least one computer readable medium or memory for holding instructions programmed according to any of the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes. Stored on any one or on a combination of computer readable media, the present disclosure includes software for controlling the computer system 1601, for driving a device or devices for implementing the invention, and for enabling the computer system 1601 to interact with a human user. Such software may include, but is not limited to, device drivers, operating systems, and applications software. Such computer readable media further includes the computer program product of the present disclosure for performing all or a portion (if processing is distributed) of the processing performed in implementing any portion of the invention.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term "computer readable medium" as used herein refers to any non-transitory medium that participates in providing instructions to the processor 1603 for execution. A computer readable medium may take many forms, including but not limited to, non- volatile media or volatile media. Non-volatile media includes, for example, optical, magnetic disks, and magneto-optical disks, such as the hard disk 1607 or the removable media drive 1108. Volatile media includes dynamic memory, such as the main memory 1604. Transmission media, on the contrary, includes coaxial cables, copper wire and fiber optics, including the wires that make up the bus 1602. Transmission media also may also take the form of acoustic or light waves, such as those generated during radio wave and infrared data communications.

Various forms of computer readable media may be involved in carrying out one or more sequences of one or more instructions to processor 1603 for execution. For example, the instructions may initially be carried on a magnetic disk of a remote computer. The remote computer can load the instructions for implementing all or a portion of the present disclosure remotely into a dynamic memory and send the instructions over a telephone line using a modem. A modem local to the computer system 1601 may receive the data on the telephone line and place the data on the bus 1602. The bus 1602 carries the data to the main memory 1604, from which the processor 1603 retrieves and executes the instructions. The instructions received by the main memory 1604 may optionally be stored on storage device 1607 or 1608 either before or after execution by processor 1603.

The computer system 1601 also includes a communication interface 1613 coupled to the bus 1602. The communication interface 1613 provides a two-way data communication coupling to a network link 1614 that is connected to, for example, a local area network (LAN) 1615, or to another communications network 1616 such as the Internet. For example, the communication interface 1613 may be a network interface card to attach to any packet switched LAN. As another example, the communication interface 1613 may be an integrated services digital network (ISDN) card. Wireless links may also be implemented. In any such implementation, the communication interface 1613 sends and receives electrical, electromagnetic or optical signals that carry digital data streams representing various types of information.

The network link 1614 typically provides data communication through one or more networks to other data devices. For example, the network link 1614 may provide a connection to another computer through a local network 1615 (e.g., a LAN) or through equipment operated by a service provider, which provides communication services through a communications network 1616. The local network 1614 and the communications network 1616 use, for example, electrical, electromagnetic, or optical signals that carry digital data streams, and the associated physical layer (e.g., CAT 5 cable, coaxial cable, optical fiber, etc.). The signals through the various networks and the signals on the network link 1614 and through the communication interface 1613, which carry the digital data to and from the computer system 1601, may be implemented in baseband signals, or carrier wave based signals.

The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1601 can transmit and receive data, including program code, through the network(s) 1615 and 1616, the network link 1614 and the communication interface 1613. Moreover, the network link 1614 may provide a connection through a LAN 1615 to a mobile device 1617 such as a personal digital assistant (PDA) laptop computer, or cellular telephone.

While aspects of the present disclosure have been described in conjunction with the specific embodiments thereof that are proposed as examples, alternatives, modifications, and variations to the examples may be made. It should be noted that, as used in the specification and the appended claims, the singular forms "a," "an," and "the" include plural referents unless the context clearly dictates otherwise.

The invention claimed is:

1. A method for generating a pain score for a patient, the method comprising:
   initiating a neuro-stimulus to the patient, the neuro-stimulus being initiated over a set of frequencies, each frequency being associated with a unique intensity, and stimulating a unique nerve fiber type of the patient;
   measuring a pupillary reflex dilation (PRD) response of the patient for the initiated neuro-stimulus;
   determining, for each nerve fiber type, a threshold response based on the measured PRD;
   determining the pain score for the patient based on each threshold response; and
   determining an appropriateness of a pharmacological intervention based on computing an area under a curve corresponding to the measured PRD response of the patient.

2. The method of claim 1, further comprising
   generating a pupillary light reflex (PLR) response signature for each drug of a plurality of drugs; and
   initiating a light stimulus to the patient and measuring a corresponding PLR response,
   wherein the PLR response is characterized by a light reflex amplitude parameter, a latency of light reflex parameter, a constriction velocity parameter, and a dilation velocity parameter.

3. The method of claim 2, wherein the plurality of drugs include ketamine, gabapentin, pregabalin, selective serotonin inhibitors, serotonin norepinephrine reuptake inhibitors, tricyclic antidepressants, and monamine oxidase inhibitors.

4. The method of claim 2, further comprising:
   detecting an onset of tolerance by repeating the measuring of the PLR response and the PRD response of the patient over a predetermined time-period.

5. The method of claim 1, wherein the set of frequencies includes a first frequency of 2000 Hz that stimulates Aβ-fiber, a second frequency of 250 Hz that stimulates Aδ-fiber, and a third frequency of 5 Hz that stimulates a C-fiber of the patient.

6. The method of claim 1, further comprising:
   determining a pain sensitivity of the patient by computing the area under the curve corresponding to the measured PRD response, the PRD response being characterized by two static parameters and at least three dynamic parameters.

7. The method of claim 6, wherein the two static parameters include a pupillary baseline dilation diameter and a peak dilation diameter, and the at least three dynamic parameters include the area under the curve, a dilation velocity, and a duration of dilation.

8. The method of claim 1, further comprising:
   identifying a type of pain experienced by the patient based on the initiated neuro-stimulus and the measured PRD response of the patient.

9. The method of claim 8, wherein the type of pain is one of a neuropathic pain and a nociceptive pain, the neuropathic pain being induced by Aβ-fiber, and the nociceptive pain being induced by Aδ-fiber and C-fiber.

10. An apparatus, comprising:
    circuitry configured to
    initiate a neuro-stimulus to a patient, the neuro-stimulus being initiated over a set of frequencies, each frequency being associated with a unique intensity, and stimulating a unique nerve fiber type of the patient,
    measure a pupillary reflex dilation (PRD) response of the patient for the initiated neuro-stimulus,
    determine, for each nerve fiber type, a threshold response based on the measured PRD response, determine a pain score for the patient based on each threshold response, and
    determine an appropriateness of a pharmacological intervention based on computing an area under a curve corresponding to the measured PRD response of the patient.

11. A non-transitory computer readable medium including computer executed instructions that when executed by a computer, cause the computer to execute a method for generating a pain score for a patient, the method comprising:
    initiating a neuro-stimulus to the patient, the neuro-stimulus being initiated over a set of frequencies, each frequency being associated with a unique intensity, and stimulating a unique nerve fiber type of the patient;
    measuring a pupillary reflex dilation (PRD) response of the patient for the initiated neuro-stimulus;
    determining, for each nerve fiber type, a threshold response based on the measured PRD response;
    determine the pain score for the patient; and
    determine an appropriateness of a pharmacological intervention based on computing an area under a curve corresponding to the measured PRD response of the patient.

12. The apparatus of claim 10, wherein the processing circuitry is further configured to
    generate a pupillary light reflex (PLR) response signature for each drug of a plurality of drugs, and
    initiate a light stimulus to the patient and measure a corresponding PLR response, wherein the PLR response is characterized by a light reflex amplitude parameter, a latency of light reflex parameter, a constriction velocity parameter, and a dilation velocity parameter.

13. The method of claim 11, further comprising generating a pupillary light reflex (PLR) response signature for each drug of a plurality of drugs; and initiating a light stimulus to the patient and measuring a corresponding PLR response, wherein the PLR response is characterized by a light reflex amplitude parameter, a latency of light reflex parameter, a constriction velocity parameter, and a dilation velocity parameter.

* * * * *